(12) United States Patent
Gan et al.

(10) Patent No.: US 9,849,077 B2
(45) Date of Patent: Dec. 26, 2017

(54) SKIN LIGHTENING COMPOSITIONS

(71) Applicant: MARY KAY INC., Addison, TX (US)

(72) Inventors: David Gan, Southlake, TX (US);
Tiffany Florence, Dallas, TX (US);
Michelle Hines, Hickory Creek, TX (US);
Patricia Jacoby, Dallas, TX (US);
Wanli Zhao, Addison, TX (US);
Julia Collier, Addison, TX (US);
Edward Chadwick, Addison, TX (US);
Mauricio Castro, Piano, TX (US);
Barbara Durkee, Carrollton, TX (US);
Daniel Ramirez, Addison, TX (US)

(73) Assignee: Mary Kay Inc., Addison, TX (US)

( * ) Notice: Subject to any disclaimer, the term of this patent is extended or adjusted under 35 U.S.C. 154(b) by 0 days.

(21) Appl. No.: 14/640,328

(22) Filed: Mar. 6, 2015

(65) Prior Publication Data
US 2015/0250709 A1 Sep. 10, 2015

Related U.S. Application Data

(60) Provisional application No. 61/950,517, filed on Mar. 10, 2014, provisional application No. 62/088,812, filed on Dec. 8, 2014.

(51) Int. Cl.
| | | |
|---|---|---|
| *A61K 8/97* | (2017.01) | |
| *A61K 8/25* | (2006.01) | |
| *A61K 8/29* | (2006.01) | |
| *A61K 8/31* | (2006.01) | |
| *A61K 8/34* | (2006.01) | |
| *A61K 8/35* | (2006.01) | |
| *A61K 8/36* | (2006.01) | |
| *A61K 8/368* | (2006.01) | |
| *A61K 8/37* | (2006.01) | |
| *A61K 8/41* | (2006.01) | |
| *A61K 8/42* | (2006.01) | |
| *A61K 8/49* | (2006.01) | |
| *A61K 8/58* | (2006.01) | |
| *A61K 8/73* | (2006.01) | |
| *A61K 8/81* | (2006.01) | |
| *A61K 8/92* | (2006.01) | |
| *A61Q 19/02* | (2006.01) | |
| *A61K 8/67* | (2006.01) | |

(52) U.S. Cl.
CPC ............... *A61K 8/97* (2013.01); *A61K 8/25* (2013.01); *A61K 8/29* (2013.01); *A61K 8/31* (2013.01); *A61K 8/345* (2013.01); *A61K 8/347* (2013.01); *A61K 8/35* (2013.01); *A61K 8/36* (2013.01); *A61K 8/368* (2013.01); *A61K 8/37* (2013.01); *A61K 8/41* (2013.01); *A61K 8/42* (2013.01); *A61K 8/494* (2013.01); *A61K 8/4926* (2013.01); *A61K 8/4973* (2013.01); *A61K 8/585* (2013.01); *A61K 8/675* (2013.01); *A61K 8/73* (2013.01); *A61K 8/738* (2013.01); *A61K 8/8141* (2013.01); *A61K 8/8158* (2013.01); *A61K 8/92* (2013.01); *A61Q 19/02* (2013.01); *A61K 2800/59* (2013.01)

(58) Field of Classification Search
CPC .......... A61K 8/97; A61K 8/41; A61K 8/4926; A61K 8/347; A61K 8/345; A61K 8/25; A61K 8/585; A61K 8/738; A61K 8/36; A61K 8/8141; A61K 8/4973; A61K 8/73; A61K 8/8158; A61K 8/368; A61K 8/42; A61K 8/37; A61K 8/35; A61K 8/92; A61K 8/31; A61K 8/29; A61K 8/494; A61K 2800/59; A61Q 19/02
See application file for complete search history.

(56) References Cited

U.S. PATENT DOCUMENTS

| | | | |
|---|---|---|---|
| 2,798,053 A | 7/1957 | Brown | 521/38 |
| 3,755,560 A | 8/1973 | Dickert et al. | 514/772.6 |
| 4,421,769 A | 12/1983 | Dixon et al. | 514/772 |
| 4,509,949 A | 4/1985 | Huang et al. | 8/558 |
| 4,599,379 A | 7/1986 | Flesher et al. | 524/801 |
| 4,628,078 A | 12/1986 | Glover et al. | 526/303.1 |
| 4,835,206 A | 5/1989 | Farrar et al. | 524/457 |
| 4,849,484 A | 7/1989 | Heard | 525/221 |
| 5,011,681 A | 4/1991 | Ciotti et al. | 510/136 |
| 5,087,445 A | 2/1992 | Haffey et al. | 424/59 |

(Continued)

FOREIGN PATENT DOCUMENTS

| | | |
|---|---|---|
| CN | 1960700 | 5/2007 |
| CN | 201010122699 | 3/2010 |

(Continued)

OTHER PUBLICATIONS

Kovacevic, Katarina. "Kelp From the sea." Published May 29, 2013. Retrieved on Jan. 18, 2016. Retrieved From the Internet <URL: http://www.americanspa.com/americanspa/spa-treatments/kelp-sea-0>.*

(Continued)

*Primary Examiner* — Anoop Singh
*Assistant Examiner* — Doan Phan
(74) *Attorney, Agent, or Firm* — Norton Rose Fulbright US LLP

(57) ABSTRACT

Disclosed are compositions and methods for their use that include a combination of *Leontopodium alpinum* extract, *Halidrys siliquosa* extract, vegetable amino acids, niacinamide, hexylresorcinol, *Pinus pinaster* extract, *Betula alba* extract, *Albizia julibrissin* bark extract, hydrolyzed *Candida saitoana* extract, *Lentinus edodes* mycelium extract, and/or *Opuntia tuna* fruit extract.

31 Claims, 9 Drawing Sheets

(56) References Cited

U.S. PATENT DOCUMENTS

| | | | |
|---|---|---|---|
| 5,100,660 A | 3/1992 | Hawe et al. | 424/78.35 |
| 5,411,741 A | 5/1995 | Zaias | 424/450 |
| 5,939,082 A | 8/1999 | Oblong et al. | 424/401 |
| 6,197,343 B1 | 3/2001 | Minami et al. | 424/489 |
| 6,863,897 B2 | 3/2005 | Love et al. | 424/401 |
| 8,236,288 B2 | 8/2012 | Mehta et al. | 424/59 |
| 8,247,405 B2 | 8/2012 | Madison | 514/215 |
| 2001/0033850 A1 | 10/2001 | Vatter et al. | 424/401 |
| 2003/0049212 A1 | 3/2003 | Robinson et al. | 424/59 |
| 2005/0019283 A1 | 1/2005 | Nonaka et al. | 424/62 |
| 2006/0008538 A1* | 1/2006 | Wu | A61K 8/368 424/705 |
| 2008/0305059 A1 | 12/2008 | Chaudhuri | 424/62 |
| 2009/0253663 A1 | 10/2009 | Akamatsu et al. | 514/171 |
| 2009/0324661 A1 | 12/2009 | Polonka et al. | 424/401 |
| 2010/0189669 A1* | 7/2010 | Hakozaki | A61K 8/347 514/1.1 |
| 2010/0203077 A1* | 8/2010 | Schnittger | A61Q 19/00 424/195.15 |
| 2010/0303854 A1* | 12/2010 | Hines | A61K 8/97 424/195.17 |
| 2011/0081305 A1 | 4/2011 | Cochran et al. | 424/59 |
| 2011/0082217 A1 | 4/2011 | Johnson et al. | 514/731 |
| 2011/0086060 A1 | 4/2011 | Bidamant et al. | 424/195.17 |
| 2011/0243983 A1 | 10/2011 | Paufique | 424/195.16 |
| 2012/0002669 A1 | 1/2012 | Dietterle et al. | 370/389 |
| 2012/0058140 A1* | 3/2012 | Ceccoli | A61K 8/64 424/195.15 |
| 2012/0128605 A1 | 5/2012 | Cochran et al. | 424/59 |
| 2012/0128613 A1 | 5/2012 | Cochran et al. | 424/62 |
| 2012/0164121 A1* | 6/2012 | Paufique | A61K 8/99 424/93.51 |
| 2012/0189684 A1 | 7/2012 | Buckley et al. | 424/443 |
| 2012/0283226 A1 | 11/2012 | Buckley et al. | 280/623 |
| 2012/0288478 A1* | 11/2012 | Florence | A61K 8/64 424/93.1 |
| 2013/0071426 A1 | 3/2013 | Serra-Baldrich et al. | 424/195.17 |
| 2013/0156873 A1 | 6/2013 | Florence et al. | |
| 2013/0195925 A1* | 8/2013 | Arshed | A61K 8/97 424/400 |

FOREIGN PATENT DOCUMENTS

| | | | |
|---|---|---|---|
| CN | 102028626 | 4/2011 | |
| EP | 2316411 | 11/2012 | |
| EP | 2522330 | 11/2015 | |
| FR | 2942136 | 8/2010 | |
| FR | WO 2013046137 A2 * | 4/2013 | A61Q 19/08 |
| KR | 1020010020354 | 10/2001 | |
| KR | 10-0443588 | 7/2004 | |
| KR | 10-0512690 | 9/2005 | |
| KR | 10-0525842 | 10/2006 | |
| KR | 1020090009865 | 2/2009 | |
| KR | 1020100096048 | 10/2010 | |
| KR | 1020100120141 | 11/2010 | |
| KR | 1020100129754 | 12/2010 | |
| KR | 1020110012224 | 2/2011 | |
| KR | 1020110011654 | 5/2013 | |
| KR | 1020070008283 | 6/2013 | |
| KR | 1020110042071 | 6/2013 | |
| NL | EP 2522330 A1 * | 11/2012 | A61K 8/347 |
| WO | WO 98/52533 | 11/1998 | |
| WO | WO 2005/004833 | 1/2005 | |
| WO | WO 2005/044214 | 5/2005 | |
| WO | WO 2006/117055 | 5/2005 | |
| WO | WO 2005/067885 | 7/2005 | |
| WO | WO 2005/094770 | 10/2005 | |
| WO | WO 2006/117055 | 11/2006 | |
| WO | WO 2007/106501 | 9/2007 | |
| WO | WO 2010/000587 | 1/2010 | |
| WO | WO 2012/003806 | 1/2010 | |
| WO | WO 2010/064878 | 6/2010 | |
| WO | WO 2012/002669 | 1/2012 | |
| WO | WO 2012/011908 | 1/2012 | |

OTHER PUBLICATIONS

MacDonald (Published Nov. 9, 2005). "Natural Ingredients in Personal Care Products." Retrieved on Jan. 18, 2016. Retrieved from the Internet <URL: http://www.happi.com/issues/2001-06/view_features/natural-ingredients-in-personal-care-products/>.*
Tsuda et al (1997). Inhibition of Tyrosinase Activity by the Anthocyanin Pigments Isolated from *Phaseolus vulgaris* L., Food Sci. Technol. Int. Tokyo, 3(1): 82-83.*
Pulse Canada—"Bean (*Phaseolus vulgaris*)". Retrieved on Oct. 12, 2016. Retrieved From the Internet <URL: http://www.pulsecanada.com/about-us/what-is-a-pulse/bean>.*
International Cosmetic Ingredient Dictionary and Handbook, 12*th* Edition, 2008, vol. 2, p. 1449.
International Cosmetic Ingredient Dictionary and Handbook, 12*th* Edition, 2008, vol. 2, pp. 1651-1652.
International Cosmetic Ingredient Dictionary and Handbook, 12*th* Edition, 2008, vol. 1, p. 1158.
International Cosmetic Ingredient Dictionary and Handbook, 12*th* Edition, 2008, vol. 2, p. 2034
International Cosmetic Ingredient Dictionary and Handbook, 12*th* Edition, 2008, vol. 1, p. 280.
International Cosmetic Ingredient Dictionary and Handbook, 12*th* Edition, 2008, vol. 1, p. 84.
International Cosmetic Ingredient Dictionary and Handbook, 12*th* Edition, 2008, vol. 2, p. 1731.
Database GNPD [Online] MINTEL; Dec. 2013 (Dec. 2013), "Whitening & Multieffect B.B Cream With Edelweiss" , XP002740353, Database Accession No. 2271200.
Database GNPD [Online] MINTEL; Sep. 2011 (Sep. 2011), "Whitening Essence", XP002740354, Database Accession No. 1625153.
International Search Report issued in PCT/US2015/019172 dated Jun. 11, 2015.
"Bluenikko Tonymoly Floria Whitening Capsule Essence", 2012. pp. 1-3. <http://www.cosdna.com/chs/cosmetic_84b584940.html>.
Search Report issued in Chinese application No. 201410188678 dated May 9, 2017 (Attorney Docket MKAY.P0539CN).
Ke, Rui "Resorcinol Derivatives—A Highly Efficient Lightening Component Will Become Popular," 2012, p. 3, <http://www.truebuty.com/whitenins-insredient-res.html>.
Wang, Jianxin et al. *The Encyclopedia of Raw Plant Materials of Cosmetics*, China Textile & Apparel Press, 2012, 401-402.

* cited by examiner

SKIN LIGHTENING COMPOSITIONS

CROSS REFERENCE TO RELATED APPLICATIONS

This application claims the benefit of U.S. Provisional Application No. 61/950,517 filed Mar. 10, 2014, and U.S. Provisional Application No. 62/088,812 filed Dec. 8, 2014, the contents of which are incorporated into the present application by reference.

BACKGROUND OF THE INVENTION

A. Field of the Invention

The present invention relates generally to compositions that can be used to improve the skin's visual appearance. In certain aspects, the compositions of the present invention can include, for example, a combination of ingredients to whiten skin, even out skin color, or treat hyperpigmentation. This combination of ingredients can be included in a wide-range of product formulations (e.g., serums, eye creams, toners, gels, masks, etc.).

B. Description of Related Art

The color in human skin is caused by the pigment melanin. Melanin is produced in special dendritic cells, melanocytes, which are found below or between the basal cells of the epidermis of the skin (U.S. Pat. No. 5,411,741). When exposed to damaging environmental factors such the ultra violet (UV) radiation of the sun, irritants, and pollution, the keratinocyte (outermost cell of the skin) releases signaling molecules, such as α-melanocyte-stimulating hormone (α-MSH), and inflammatory cytokines. These hormones trigger melanocytes to produce melanin (Garcia-Borron et al., 2005).

Typical pigmentation is characterized by an even, uniform coloration of the skin. Many individuals have excess melanin pigmentation or a hyperpigmentation patch which can cause pigmentary variation or abnormal pigmentation of the skin. This may lead to unwanted freckles or dark spots such as senile lentigo, liver spots, melasma, brown or age spots, vitiligo, sunburn pigmentation, post-inflammatory hyperpigmentation due to abrasion, burns, wounds or dermatitis, phototoxic reaction and other similar small, fixed pigmented lesions. It is often desirable to lighten these areas or even out the appearance of irregularly pigmented areas of skin. Individuals may also wish to increase fairness or reduce the overall level of pigmentation in the skin. In either case, the hyperpigmentation is usually viewed as cosmetically undesirable and individuals often wish to lighten the skin.

In some instances, the use of one skin lightening ingredient may not be effective for individuals with significant hyperpigmentation, freckles, or age spots, for example. Additionally, previous attempts to combine various skin lightening ingredients have been ineffective, and in some instance, have produced negative results (Talwar 1993).

SUMMARY OF THE INVENTION

The present invention overcomes deficiencies in the art by providing an effective and natural alternative to lighten skin, reduce the appearance of uneven skin tone, and/or treat melasmic skin. The solution is premised on a discovery of a combination of ingredients—*Leontopodium alpinum* extract, *Halidrys siliquosa* extract, vegetable amino acids, niacinamide, hexylresorcinol, *Pinus pinaster* extract, *Betula alba* extract, *Albizia julibrissin* bark extract, hydrolyzed *Candida saitoana* extract, *Lentinus edodes* mycelium extract, and/or *Opuntia tuna* fruit extract—that can be used for improving the skin's visual appearance, whitening or lightening the skin's color or tone, treating hyperpigmentation and other related disorders, and evening out a person's skin tone. This combination of ingredients can be used in a variety of product formulations (e.g., toners, cleansers, emulsions such as lotions or creams, masks, gels, etc.).

In one instance, there is disclosed a topical skin composition comprising an effective amount of a combination of *Leontopodium alpinum* extract, *Halidrys siliquosa* extract, vegetable amino acids, and niacinamide. Alternatively, one or any combination said ingredients can be used in the compositions of the present invention. The amounts of the ingredients within the composition can vary (e.g., amounts can be as low as 0.000001% to as high as 80% w/w or any range therein). In one instance, the composition includes 0.001 to 0.1% by weight of *Leontopodium alpinum* extract, 0.1 to 1.0% by weight of *Halidrys siliquosa* extract, 0.1 to 1.0% by weight of vegetable amino acids, and 1 to 5% by weight of niacinamide. In some aspects, the composition further comprises water. In one instance, the composition includes 70 to 80% by weight of water. In some aspects, disclosed are methods of applying any of the topical skin compositions disclosed herein comprising applying said composition to skin. In some aspects, disclosed are methods of lightening skin, reducing the appearance of uneven skin tone, or treating melasmic skin comprising applying an effective amount of any of the topical skin compositions disclosed herein to skin.

In another aspect, there is disclosed a topical skin composition comprising any one of, any combination of, or all of *Leontopodium alpinum* extract, *Halidrys siliquosa* extract, vegetable amino acids, niacinamide, hexylresorcinol, *Pinus pinaster* extract, and *Betula alba* extract. The amounts of the ingredients within the composition can vary (e.g., amounts can be as low as 0.000001% to as high as 60% w/w or any range therein). In one instance, the composition includes 0.001 to 0.1% by weight of *Leontopodium alpinum* extract, 0.1 to 1.0% by weight of *Halidrys siliquosa* extract, 0.1 to 1.0% by weight of vegetable amino acids, 1 to 5% by weight of niacinamide, 0.1 to 0.5% by weight of hexylresorcinol, 0.001 to 0.1% by weight of *Pinus pinaster* extract, and 0.001 to 0.1% by weight of *Betula alba* extract. In some aspects, the composition further comprises water. In one instance, the composition includes 70 to 80% by weight of water. In some embodiments, the composition further includes butylene glycol, glycerin, silica, cyclopentasiloxane, dimethicone, disodium EDTA, caprylyl glycol, 1,2-hexanediol, hydroxypropyl cyclodextrin; and potassium sorbate. In one instance, the composition includes those ingredients in the following amounts: 3 to 6% by weight of butylene glycol, 3 to 6% by weight of glycerin, 1 to 5% by weight of silica, 1 to 4% by weight of cyclopentasiloxane, 1 to 3% by weight of dimethicone, 0.1 to 0.5% by weight of disodium EDTA, 0.1 to 0.5% by weight of caprylyl glycol, 0.1 to 0.5% by weight of 1,2-hexanediol, 0.01 to 0.5% by weight of hydroxypropyl cyclodextrin, and 0.001 to 0.05% by weight of potassium sorbate. In another instance, the composition further includes ammonium acryloyldimethyltaurate/VP copolymer, polysorbate 20, acrylates/C10-30 alkyl acrylate crosspolymer, triethanolamine, and xanthan gum. In yet another instance, the composition includes the those ingredients in the following amounts: 0.1 to 1% by weight of ammonium acryloyldimethyltaurate/VP copolymer, 0.1 to 0.5% by weight of polysorbate 20, 0.1 to 0.5% by weight of acrylates/C10-30 alkyl acrylate crosspolymer, 0.1 to 0.5% by weight of triethanolamine, and 0.01 to 0.2% by weight of xanthan gum.

In another aspect, there is disclosed a topical skin composition comprising any one of, any combination of, or all of *Leontopodium alpinum* extract, *Halidrys siliquosa* extract, vegetable amino acids, niacinamide, and *Albizia julibrissin* bark extract. The amounts of the ingredients within the composition can vary (e.g., amounts can be as low as 0.000001% to as high as 60% w/w or any range therein). In one instance, the composition includes 0.001 to 0.1% by weight of *Leontopodium alpinum* extract, 0.1 to 1.0% by weight of *Halidrys siliquosa* extract, 0.1 to 1.0% by weight of vegetable amino acids, 1 to 5% by weight of niacinamide, and 0.5 to 2.0% by weight of *Albizia julibrissin* bark extract. In some aspects, the composition further comprises water. In one instance, the composition includes 70 to 80% by weight of water. In some embodiments, the composition further includes glycerin, dimethicone, octyldodecanol, triethanolamine, polyacrylamide, disodium EDTA, laureth-7, cyclohexasiloxane, sodium benzoate, and iodopropynyl butylcarbamate. In one instance, the composition includes those ingredients in the following amounts: 8 to 15% by weight of glycerin, 3 to 6% by weight of dimethicone, 0.1 to 1.5% by weight of octyldodecanol, 0.1 to 1.5% by weight of tirethanolamine, 0.1 to 1.5% by weight of polyacrylamide, 0.01 to 0.2% by weight of disodium EDTA, 0.01 to 0.2% by weight of laureth-7, 0.01 to 0.2% by weight of cyclohexasiloxane, 0.001 to 0.2% by weight of sodium benzoate, and 0.001 to 0.2% by weight of iodopropynyl butylcarbamate.

In another aspect, there is disclosed a topical skin composition comprising any one of, any combination of, or all of *Leontopodium alpinum* extract, *Halidrys siliquosa* extract, vegetable amino acids, niacinamide, and hydrolyzed *Candida saitoana* extract. The amounts of the ingredients within the composition can vary (e.g., amounts can be as low as 0.000001% to as high as 85% w/w or any range therein).

In another aspect, there is disclosed a topical skin composition comprising any one of, any combination of, or all of *Leontopodium alpinum* extract, *Halidrys siliquosa* extract, vegetable amino acids, niacinamide, and *Lentinus edodes* mycelium extract. The amounts of the ingredients within the composition can vary (e.g., amounts can be as low as 0.000001% to as high as 85% w/w or any range therein).

In another aspect, there is disclosed a topical skin composition comprising any one of, any combination of, or all of *Leontopodium alpinum* extract, *Halidrys siliquosa* extract, vegetable amino acids, niacinamide, *Lentinus edodes* mycelium extract, and *Opuntia tuna* fruit extract. The amounts of the ingredients within the composition can vary (e.g., amounts can be as low as 0.000001% to as high as 85% w/w or any range therein).

In another aspect, there is disclosed a topical skin composition comprising any one of, any combination of, or all of *Leontopodium alpinum* extract, *Halidrys siliquosa* extract, vegetable amino acids, and/or *Opuntia tuna* fruit extract. The amounts of the ingredients within the composition can vary (e.g., amounts can be as low as 0.000001% to as high as 85% w/w or any range therein).

In some embodiments, the disclosed combination of ingredients is used in a moisturizer, a face freshener, a day cream, a night cream, a cloth face or eye mask, or a hydrogel mask product, a face mask, or a cleanser formulation.

Also disclosed are the following Embodiments 1 to 46 of the present invention. Embodiment 1 is a topical skin composition comprising an effective amount of *Leontopodium alpinum* extract, *Halidrys siliquosa* extract, vegetable amino acids, and niacinamide, wherein the composition is capable of whitening or lightening skin. Embodiment 2 is the topical skin composition of Embodiment 1, comprising 0.001 to 0.1% by weight of *Leontopodium alpinum* extract, 0.1 to 1.0% by weight of *Halidrys siliquosa* extract, 0.1 to 1.0% by weight of vegetable amino acids, and 1 to 5% by weight of niacinamide. Embodiment 3 is the topical skin composition of Embodiment 1, wherein the composition further includes water. Embodiment 4 is the topical skin composition of Embodiment 3, comprising 55 to 80% by weight of water. Embodiment 5 is the topical skin composition of Embodiment 1, wherein the composition further includes *Opuntia tuna* fruit extract. Embodiment 6 is the topical skin composition of Embodiment 5, wherein the composition comprises 0.0001 to 0.015% by weight of *Opuntia tuna* fruit extract. Embodiment 7 is the topical skin composition of Embodiment 1, wherein the composition further includes: hexylresorcinol, *Pinus pinaster* extract, and *Betula alba* extract. Embodiment 8 is the topical skin composition of Embodiment 7, wherein the composition includes: 0.1 to 0.5% by weight of hexylresorcinol, 0.001 to 0.1% by weight of *Pinus pinaster* extract, and 0.001 to 0.1% by weight of *Betula alba* extract. Embodiment 9 is the topical skin composition of Embodiment 7, wherein the composition further includes: butylene glycol, glycerin, silica, cyclopentasiloxane, dimethicone, disodium EDTA, caprylyl glycol, 1,2-hexanediol, hydroxypropyl cyclodextrin, and potassium sorbate. Embodiment 10 is the topical skin composition of Embodiment 9, wherein the composition includes: 3 to 6% by weight of butylene glycol, 3 to 6% by weight of glycerin, 1 to 5% by weight of silica, 1 to 4% by weight of cyclopentasiloxane, 1 to 3% by weight of dimethicone, 0.1 to 0.5% by weight of disodium EDTA, 0.1 to 0.5% by weight of caprylyl glycol, 0.1 to 0.5% by weight of 1,2-hexanediol, 0.01 to 0.5% by weight of hydroxypropyl cyclodextrin, and 0.001 to 0.05% by weight of potassium sorbate. Embodiment 11 is the topical skin composition of Embodiment 9, wherein the composition further includes: ammonium acryloyldimethyltaurate/VP copolymer, polysorbate 20, acrylates/C10-30 alkyl acrylate crosspolymer, triethanolamine, and xanthan gum. Embodiment 12 is the topical skin composition of Embodiment 11, wherein the composition includes: 0.1 to 1% by weight of ammonium acryloyldimethyltaurate/VP copolymer, 0.1 to 0.5% by weight of polysorbate 20, 0.1 to 0.5% by weight of acrylates/C10-30 alkyl acrylate crosspolymer, 0.1 to 0.5% by weight of triethanolamine, and 0.01 to 0.2% by weight of xanthan gum. Embodiment 13 is the topical skin composition of Embodiment 1, wherein the composition further includes *Albizia julibrissin* bark extract. Embodiment 14 is the topical skin composition of Embodiment 13, wherein the composition includes 0.5 to 2.0% by weight of *Albizia julibrissin* bark extract. Embodiment 15 is the topical skin composition of Embodiment 13, wherein the composition further includes: glycerin, dimethicone, octyldodecanol, triethanolamine, polyacrylamide, disodium EDTA, laureth-7, cyclohexasiloxane, sodium benzoate, and iodopropynyl butylcarbamate. Embodiment 16 is the topical skin composition of Embodiment 15, wherein the composition includes: 8 to 15% by weight of glycerin, 3 to 6% by weight of dimethicone, 0.1 to 1.5% by weight of octyldodecanol, 0.1 to 1.5% by weight of triethanolamine, 0.1 to 1.5% by weight of polyacrylamide, 0.01 to 0.2% by weight of disodium EDTA, 0.01 to 0.2% by weight of laureth-7, 0.01 to 0.2% by weight of cyclohexasiloxane, 0.001 to 0.2% by weight of sodium benzoate, and 0.001 to 0.2% by weight of iodopropynyl butylcarbamate. Embodiment 17 is the topical skin composition of Embodiment 1, wherein the composition further includes hydrolyzed *Candida saitoana* extract. Embodiment 18 is the topical skin composition of Embodiment 1, wherein the composition further includes *Lentinus edodes* mycelium extract. Embodiment 19 is the topical skin composition of Embodiment 18, comprising 0.01 to 3% by weight of *Lentinus edodes* mycelium extract. Embodiment 20 is the topical skin composition of Embodiment 18, wherein the composition further includes: isononyl isononanoate, glycerin, octisalate, alcohol denatured, octocrylene, avobenzone, butylene glycol, cyclopentasiloxane, cetearyl glucoside, cetyl alcohol, dimethicone, glyceryl stearate, PEG-100 stearate, phenoxyethanol, caprylyl glycol, ammonium acryloyldimethyltaurate/vp copolymer, magnesium aluminum silicate, xanthan gum, and disodium EDTA. Embodiment 21 is the topical skin composition of Embodiment 20, wherein the composition includes: 3 to 9% by weight of isononyl isononanoate, 3 to 9% by weight of glycerin, 3 to 9% by weight of octisalate, 2 to 8% by weight of alcohol denatured, 1 to 7% by weight of octocrylene, 1 to 7% by weight of avobenzone, 0.5 to 6% by weight of butylene glycol, 0.5 to 6% by weight of cyclopentasiloxane, 0.5 to 6% by weight of cetearyl glucoside, 0.1 to 4% by weight of cetyl alcohol, 0.1 to 4% by weight of dimethicone, 0.1 to 4% by weight of glyceryl stearate, 0.1 to 4% by weight of PEG-100 stearate, 0.1 to 4% by weight of phenoxyethanol, 0.1 to 1.5% by weight of caprylyl glycol, 0.1 to 1.5% by weight of ammonium acryloyldimethyltaurate/vp copolymer, 0.1 to 1.5% by weight of magnesium aluminum silicate, 0.1 to 0.5% by weight of xanthan gum, and 0.01 to 0.5% by weight of disodium EDTA. Embodiment 22 is the topical skin composition of Embodiment 18, wherein the composition further includes: petrolatum, glycerin, octyldodecyl oleate, pentylene glycol, hydrogenated polydecene, glyceryl stearate, arachidyl alcohol, PEG-100 stearate, ammonium acryloyldimethyltaurate/vp copolymer, cetearyl alcohol, benzyl alcohol, synthetic wax, behenyl alcohol, cetearyl glucoside, microcrystalline wax/cire microcrystalline, phenoxyethanol, arachidyl glucoside, xanthan gum, ceteareth-20, disodium EDTA, tocopheryl acetate, and triethanolamine. Embodiment 23 is the topical skin composition of Embodiment 22, wherein the composition includes: 5 to 11% by weight of petrolatum, 3 to 11% by weight of glycerin, 1 to 7% by weight of octyldodecyl oleate, 1 to 7% by weight of pentylene glycol, 0.5 to 6% by weight of hydrogenated polydecene, 0.5 to 6% by weight of glyceryl stearate, 0.1 to 4% by weight of arachidyl alcohol, 0.1 to 4% by weight of PEG-100 stearate, 0.1 to 4% by weight of ammonium acryloyldimethyltaurate/vp copolymer, 0.1 to 4% by weight of cetearyl alcohol, 0.1 to 4% by weight of benzyl alcohol, 0.1 to 4% by weight of synthetic wax, 0.1 to 4% by weight of behenyl alcohol, 0.1 to 4% by weight of cetearyl glucoside, 0.1 to 1.5% by weight of microcrystalline wax/cire microcrystalline, 0.1 to 1.5% by weight of phenoxyethanol, 0.1 to 1.5% by weight of arachidyl glucoside, 0.1 to 1% by weight of xanthan gum, 0.01 to 0.5% by weight of ceteareth-20, 0.01 to 0.5% by weight of disodium EDTA, 0.01 to 0.3% by weight of tocopheryl acetate, and 0.01 to 0.3% by weight of triethanolamine. Embodiment 24 is the topical skin composition of Embodiment 18, wherein the composition further includes: glycerin, butylene glycol, divinyldimethicone/dimethicone copolymer, methyl gluceth-20, dimethicone, biosaccharide gum-1, phenoxyethanol, dimethicone/vinyl dimethicone crosspolymer, triethanolamine, acrylates/C10-30 alkyl acrylate crosspolymer, panthenol, C12-13 pareth-23, C12-13 pareth-3, disodium EDTA, dipotassium glycyrrhizate, and xanthan gum. Embodiment 25 is the topical skin composition of Embodiment 24, wherein the composition includes: 5 to 15% by weight of glycerin, 1 to 10% by weight of butylene glycol, 1 to 10% by weight of divinyldimethicone/dimethicone copolymer, 1 to 10% by weight of methyl gluceth-20, 0.1 to 5% by weight of dimethicone, 0.1 to 5% by weight of biosaccharide gum-1, 0.1 to 2% by weight of phenoxyethanol, 0.1 to 5% by weight of dimethicone/vinyl dimethicone crosspolymer, 0.1 to 1% by weight of triethanolamine, 0.1 to 1% by weight of acrylates/C10-30 alkyl acrylate crosspolymer, 0.1 to 1% by weight of panthenol, 0.05 to 0.5% by weight of C12-13 pareth-23, 0.05 to 0.5% by weight of C12-13 pareth-3, 0.01 to 0.5% by weight of disodium EDTA, 0.01 to 0.5% by weight of dipotassium glycyrrhizate, and 0.01 to 0.5% by weight of xanthan gum. Embodiment 26 is the topical skin composition of Embodiment 18, wherein the composition further includes: glycerin, titanium dioxide, butylene glycol, biosaccharide gum-1, polyacrylamide, hydrolyzed jojoba esters, propylene glycol, C13-14 isoparaffin, diazolidinyl urea, sodium polyacrylate, benzyl alcohol, laureth-7, jojoba esters, and methylparaben. Embodiment 27 is the topical skin composition of Embodiment 26, wherein the composition comprises: 5 to 25% by weight of glycerin, 3 to 15% by weight of titanium dioxide, 1 to 10% by weight of butylene glycol, 0.1 to 3% by weight of biosaccharide gum-1, 0.1 to 3% by weight of polyacrylamide, 0.1 to 3% by weight of hydrolyzed jojoba esters, 0.1 to 3% by weight of propylene glycol, 0.1 to 3% by weight of C13-14 isoparaffin, 0.1 to 1% by weight of diazolidinyl urea, 0.1 to 1% by weight of sodium polyacrylate, 0.05 to 0.5% by weight of benzyl alcohol, 0.05 to 0.5% by weight of laureth-7, 0.05 to 0.5% by weight of jojoba esters, and 0.05 to 0.5% by weight of methylparaben. Embodiment 28 is a topical skin composition comprising an effective amount of *Leontopodium alpinum* extract, *Halidrys siliquosa* extract, and niacinamide, wherein the composition is capable of whitening or lightening skin. Embodiment 29 is the topical skin composition of Embodiment 28, comprising 0.001 to 0.1% by weight of *Leontopodium alpinum* extract, 0.1 to 1.0% by weight of *Halidrys siliquosa* extract, and 1 to 5% by weight of niacinamide. Embodiment 30 is the topical skin composition of Embodiment 28, wherein the composition further includes water. Embodiment 31 is the topical skin composition of Embodiment 30, comprising 70 to 80% by weight of water. Embodiment 32 is the topical skin composition of Embodiment 28, wherein the composition further includes *Opuntia tuna* fruit extract. Embodiment 33 is the topical skin composition of Embodiment 32, wherein the composition comprises 0.0001 to 0.015% by weight of *Opuntia tuna* fruit extract. Embodiment 34 is the topical skin composition of Embodiment 28, wherein the composition further includes: butylene glycol, biosaccharide gum-1, glycerin, PPG-5-ceteth-20, phenoxyethanol, bis-PEG/PPG-20/20 dimethicone, hydroxypropyl cyclodextrin, benzyl alcohol, disodium EDTA, dipotassium glycyrrhizate, ethylhexylglycerin, and triethanolamine. Embodiment 35 is the topical skin composition of Embodiment 34, wherein the composition further includes: 6 to 25% by weight of butylene glycol, 1 to 7% by weight of biosaccharide gum-1, 0.1 to 5% by weight of glycerin, 0.1 to 4% by weight of PPG-5-ceteth-20, 0.1 to 3% by weight of phenoxyethanol, 0.1 to 1.5% by weight of bis-PEG/PPG-20/20 dimethicone, 0.01 to 1.5% by weight of hydroxypropyl cyclodextrin, 0.01 to 1.5% by weight of benzyl alcohol, 0.01 to 1.5% by weight of disodium EDTA, 0.01 to 1.5% by weight of dipotassium glycyrrhizate, 0.01 to 1.5% by weight of ethylhexylglycerin, and 0.005 to 1% by weight of triethanolamine. Embodiment 36 is a topical skin composition comprising an effective amount of *Leontopodium alpinum* extract, *Halidrys siliquosa* extract, and vegetable amino acids, wherein the composition is capable of whitening or lightening skin. Embodiment 37 is the topical skin composition of Embodiment 36, comprising 0.0005 to 0.01% by weight of *Leontopodium alpinum* extract, 0.01 to 0.1% by weight of *Halidrys siliquosa* extract, and 0.005 to 0.1% by weight of vegetable amino acids. Embodiment 38 is the topical skin composition of Embodiment 36, wherein the composition further includes water. Embodiment 39 is the topical skin composition of Embodiment 38, comprising 5 to 40% by weight of water. Embodiment 40 is the topical skin composition of Embodiment 36, wherein the composition further includes *Opuntia tuna* fruit extract. Embodiment 41 is the topical skin composition of Embodiment 40, wherein the composition comprises 0.0001 to 0.015% by weight of *Opuntia tuna* fruit extract. Embodiment 42 is the topical skin composition of Embodiment 36, wherein the composition further includes: glycerin, potassium stearate, dipropylene glycol, sorbitol, potassium myristate, myristic acid, glyceryl stearate SE, PEG-60 glyceryl isostearate, stearic acid, sodium methyl cocoyl taurate, PEG-32, potassium laurate, glycol stearate, benzyl alcohol, PEG-6, polyquaternium-7, lauric acid, sodium chloride, PEG-4 laurate, and ethylene brassylate. Embodiment 43 is the topical skin composition of Embodiment 42, wherein the composition includes: 10 to 40% by weight of glycerin, 10 to 40% by weight of potassium stearate, 3 to 15% by weight of dipropylene glycol, 1 to 10% by weight of sorbitol, 1 to 10% by weight of potassium myristate, 1 to 10% by weight of myristic acid, 1 to 5% by weight of glyceryl stearate SE, 1 to 5% by weight of PEG-60 glyceryl isostearate, 1 to 5% by weight of stearic acid, 0.5 to 3% by weight of sodium methyl cocoyl taurate, 0.5 to 3% by weight of PEG-32, 0.5 to 3% by weight of potassium laurate, 0.5 to 3% by weight of glycol stearate, 0.1 to 3% by weight of benzyl alcohol, 0.1 to 3% by weight of PEG-6, 0.1 to 1.5% by weight of polyquaternium-7, 0.1 to 1.5% by weight of lauric acid, 0.1 to 1.5% by weight of sodium chloride, 0.1 to 1% by weight of PEG-4 laurate, and 0.05 to 1% by weight of ethylene brassylate. Embodiment 44 is the topical skin composition of Embodiment 42, wherein the composition is formulated as a cleanser. Embodiment 45 is a method of inhibiting melanogenesis, melanosome transfer, and/or glycation comprising topically applying the composition of any one of Embodiments 1 to 44 to skin in need thereof, wherein said composition inhibits melanogenesis, melanosome transfer, or glycation. Embodiment 46 is the method of Embodiment 45, wherein the composition is applied to dark spots on skin, uneven skin, or hyperpigmented skin.

The compositions of the present invention can also include any one of, any combination of, or all of the following additional ingredients: water, a chelating agent, a moisturizing agent, a preservative, a thickening agent, a silicone containing compound, an essential oil, a structuring agent, a vitamin, a pharmaceutical ingredient, or an antioxidant, or any combination of such ingredients or mixtures of such ingredients. In certain aspects, the composition can include at least two, three, four, five, six, seven, eight, nine, ten, or all of these additional ingredients identified in the previous sentence. Non-limiting examples of these additional ingredients are identified throughout this specification and are incorporated into this section by reference. The amounts of such ingredients can range from 0.0001% to 99.9% by weight or volume of the composition, or any integer or range in between as disclosed in other sections of this specification, which are incorporated into this paragraph by reference.

Also disclosed are methods of inhibiting melanogenesis, melanosome transfer, and/or glycation comprising topically applying any said composition to skin in need thereof, wherein said composition inhibits melanogenesis, melanosome transfer, or glycation. In some aspects, said compositions are applied to dark spots on skin, uneven skin, or hyperpigmented skin.

Kits that include the compositions of the present invention are also contemplated. In certain embodiments, the composition is comprised in a container. The container can be a bottle, dispenser, or package. The container can dispense a pre-determined amount of the composition. In certain aspects, the compositions is dispensed in a spray, dollop, or liquid. The container can include indicia on its surface. The indicia can be a word, an abbreviation, a picture, or a symbol.

It is also contemplated that the compositions disclosed throughout this specification can be used as a leave-on or rinse-off composition. By way of example, a leave-on composition can be one that is topically applied to skin and remains on the skin for a period of time (e.g., at least 5, 6, 7, 8, 9, 10, 20, or 30 minutes, or at least 1, 2, 3, 4, 5, 6, 7, 8, 9, 10, 11, 12, 13, 14, 15, 16, 17, 18, 19, 20, 21, 22, 23 or 24 hours, or overnight or throughout the day). Alternatively, a rinse-off composition can be a product that is intended to be applied to the skin and then removed or rinsed from the skin (e.g., with water) within a period of time such as less than 5, 4, 3, 2, or 1 minute. An example of a rinse of composition can be a skin cleanser, shampoo, conditioner, or soap. An example of a leave-on composition can be a skin moisturizer, sunscreen, mask, overnight cream, or a day cream.

It is contemplated that any embodiment discussed in this specification can be implemented with respect to any method or composition of the invention, and vice versa. Furthermore, compositions of the invention can be used to achieve methods of the invention.

In one embodiment, compositions of the present invention can be pharmaceutically or cosmetically elegant or can have pleasant tactile properties. "Pharmaceutically elegant," "cosmetically elegant," and/or "pleasant tactile properties" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

"Topical application" means to apply or spread a composition onto the surface of lips or keratinous tissue. "Topical skin composition" includes compositions suitable for topical application on lips or keratinous tissue. Such compositions are typically dermatologically-acceptable in that they do not have undue toxicity, incompatibility, instability, allergic response, and the like, when applied to lips or skin. Topical skin care compositions of the present invention can have a selected viscosity to avoid significant dripping or pooling after application to skin.

"Keratinous tissue" includes keratin-containing layers disposed as the outermost protective covering of mammals and includes, but is not limited to, lips, skin, hair and nails.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting" or "reducing" or any variation of these terms includes any measurable decrease or complete inhibition to achieve a desired result. The terms "promote" or "increase" or any variation of these terms includes any measurable increase or production of a protein or molecule (e.g., matrix proteins such as fibronectin, laminin, collagen, or elastin or molecules such as hyaluronic acid) to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. With respect to the transitional phase "consisting essentially of," in one non-limiting aspect, a basic and novel characteristic of the compositions and methods disclosed in this specification includes the compositions' abilities to reduce or prevent symptoms associated with sensitive skin (e.g., erythema) from appearing on a user's skin.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

Figure 1:
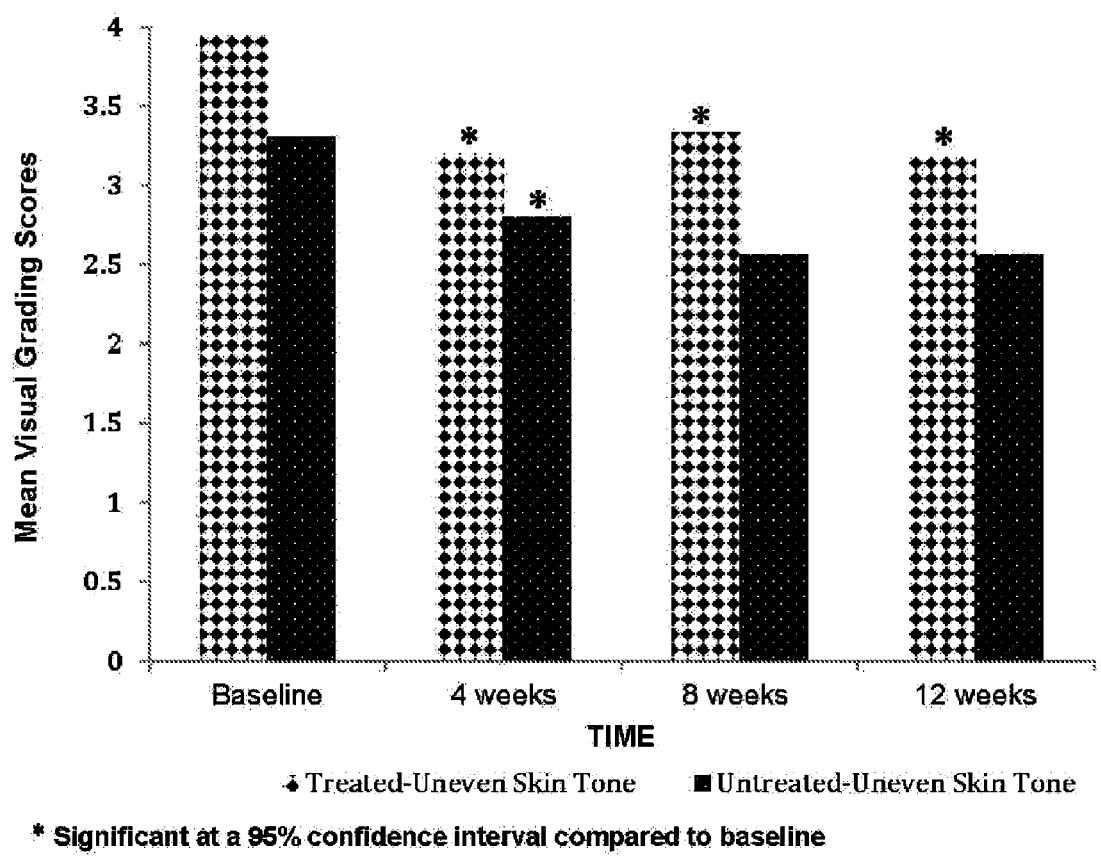
FIG. 1 Results of the visual grading of the treated and untreated groups for uneven skin tone at baseline and 4, 8, and 12 weeks.

Melanocytes are found in the basal layer of the epidermis. When exposed to damaging environmental factors such the ultra violet (UV) radiation of the sun, irritants, and pollution, the keratinocyte (outermost cell of the skin) releases signaling molecules, such as α-melanocyte-stimulating hormone (α-MSH), and inflammatory cytokines. These hormones trigger melanocytes to produce pigment known as melanin (Garcia-Borron et al., 2005). Tyrosine is a precursor molecule to melanin synthesis. It requires the enzyme tyrosinase (TYR) to change tyrosine into melanin. This reaction occurs in the melanosome, as it becomes fully matured it is filled with melanin. (Goldsmith, 1991). During this maturation process, glutathione (GSH) influences the type of melanin produced. GSH, while mostly known for its detoxification function, also shifts the production of eumelanin (dark) to pheomelanin (light). Melanocytes have dendrite structures that transfer melanosomes to the keratinocyte. (Seiberg, 2001). Damage from prolong exposure to UV rays, free radicals and irritants lead to excessive production of melanin by the melanocyte. This unregulated production of melanin leads to dark spot formation, and uneven skin tone (Bastiaens et al, 2004).

The compositions and methods of the present invention can be used, for example, for improving the skin's visual appearance, whitening or lightening the skin's color or tone, treating hyperpigmentation and other related disorders, and evening out a person's skin tone. In certain embodiments, the compositions of the present invention can include a combination of ingredients that can be used to lighten or whiten skin. These and other non-limiting aspects of the present invention are discussed in further detail in the following sections.

These and other non-limiting aspects of the present invention are provided in the following subsections.

A. Combination of Ingredients

The present invention is premised on a discovery of a combination of ingredients—*Leontopodium alpinum* extract, *Halidrys siliquosa* extract, vegetable amino acids, niacinamide, hexylresorcinol, *Pinus pinaster* extract, *Betula alba* extract, *Albizia julibrissin* bark extract, hydrolyzed *Candida saitoana* extract, *Lentinus edodes* mycelium extract, and/or *Opuntia tuna* fruit extract—that can be used to improve the skin's visual appearance, whiten or lighten the skin's color or tone, treat hyperpigmentation and other related disorders, and even out a person's skin tone. These ingredients are discussed in more detail below.

*Leontopodium alpinum* Extract:

Also known as edelweiss, *Leontopodium alpinum* is native to remote mountain areas such as the Alps. This ingredient is commercially available from a variety of sources (see, e.g., CTFA, Volume 2, page 1449, which is incorporated by reference). An exemplary source can be obtained from Carrubba Inc. (Milford, Conn. USA) under the trade name Edelweiss Extract M5768. It has been discovered that this ingredient can be used to reduce the production of melanin in skin cells (See Example 1).

*Halidrys siliquosa* Extract:

Native to the British Isles and Europe, the extract is a skin conditioner. This ingredient is commercially available from a variety of sources. An exemplary source can be obtained from Biosil (FRANCE) under the trade name Lightoceane®. It has been discovered that this algae extract targets melanin production and helps inhibit the appearance of melanin on the skin's surface by reducing the transfer of melanin to the skin (See Example 1).

Vegetable Amino Acids (Navy Bean):

The navy bean is produced from the common bean plant (*Phaseolus vulgaris*). The navy bean is a small white bean that is produced worldwide from North America to Europe to Africa to Asia, and it is different from green beans, anasazi beans, black beans, cranberry or borlotti beans, chickpeas, lentil beans, pink beans, pinto beans, red kidney beans, shell beans, and yellow beans. Vegetable amino acids (navy bean) have been discovered to significantly improve the brightness of the skin. They have also been shown to improve the overall evenness of skin tone and reduce the visible contrast of dark spots on the skin as it targets melanin production (See Examples 1 and 2). Navy bean extract is commercially available from a wide range of sources. For instance, Carrubba Inc. (Milford, Conn. USA) produces an aqueous liquid navy bean extract that can be used in the context of the present invention. Also, InfraReady Products (1998) Ltd. (CANADA) produces a powdered navy been extract that can also be used in the context of the present invention.

Niacinamide:

Also known nicotinamide, 3-Pyridinecarboxamide, or Vitamin $B_3$, it is an organic compound known to exhibit skin conditioning benefits when used in cosmetic compositions. Niacinamide has the following chemical formula:

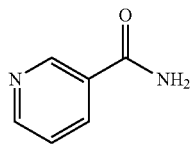

This ingredient is commercially available from a variety of sources (see, e.g., CTFA, Volume 2, pages 1651-1652, which is incorporated by reference). It has been discovered that this ingredient can be used to provide added skin brightening benefits and to inhibit melanin transfer to the skin (See Example 1).

Hexylresorcinol:

Glutathione (GSH), comprised of three amino acids, is vital to the skin's detoxification process. As we age, our body's natural production of GSH decreases. Stress and environmental pollutants also depletes its levels. GSH can also influence the melanocyte to produce lighter melanin. Hexylresorcinol is shown to boost glutathione in skin. It is also shown to target melanin production and help prevent protein glycation. Accumulation of glycated proteins in skin can lead to discoloration, in addition to damaging the skin. (See Example 1). This ingredient is commercially available from a variety of sources (see, e.g., CTFA, Volume 1, page 1158, which is incorporated by reference). An exemplary source can be obtained from Syntheon Limited (USA) under the trade name Synovea® HR.

*Pinus pinaster* Bark/Bud Extract:

Native to the Mediterranean, the Maritime Pine is a known source of antioxidants such as flavonoids, catechins, proanthocyanidins, and phenolic acids. This ingredient is commercially available from a variety of sources (see, e.g., CTFA, Volume 2, page 2034, which is incorporated by reference). An exemplary source can be obtained from Carrubba Inc. (Milford, Conn. USA). It has been discovered that this ingredient can be used to reduce the production of melanin in skin cells (See Example 1).

*Betula alba* Leaf Extract:

Native to Northern Europe, and Iceland, the extract of the White Birch is known for its purifying and detoxifying effects, encourages the excretion of fluids and promotes metabolic activities. This ingredient is commercially available from a variety of sources (see, e.g., CTFA, Volume 1, page 280, which is incorporated by reference). An exemplary source can be obtained from Carrubba Inc. (Milford, Conn. USA). It has been discovered that this ingredient can be used to reduce the production of melanin in skin cells (See Example 1).

*Albizia julibrissin* Bark Extract:

Also known as the Persian or pink silk tree, *Albizia julibrissin* is native to southwestern and eastern Asia. This ingredient is commercially available from a variety of sources (see, e.g., CTFA, Volume 1, page 84, which is incorporated by reference). An exemplary source can be obtained from Sederma (FRANCE) under the trade name Prodizia™.

Hydrolyzed *Candida saitoana* Extract:

An isolated and purified form of *Candida saitoana*, a fungi obtained from a fermentation process, the extract is designed to target proteasome and autophagic pathways, the skin's natural detoxification mechanisms. This ingredient is commercially available from a variety of sources. An exemplary source can be obtained from Silab (FRANCE) under the trade name Celldetox®.

*Lentinus edodes* Mycelium Extract:

Also known as *Lentinus enodes* and shiitake, *Lentinus edodes* mycelium is a wood-decaying basidiomycetes growing on fallen wood of a wide variety of deciduous trees throughout east Asia and as far south as Australia. It is capable of providing antioxidant and anti-inflammatory benefit for skin. It is also a source of kojic acid, which is beneficial to even and lighten skin tone. This ingredient is commercially available from a variety of sources. An exemplary source can be obtained from Actives International (USA) under the trade name ViaFerm White.

*Opuntia tuna* Fruit Extract:

Also commonly known as prickly pear, *Opuntia tuna* is the fruit of a family of cactus native to the Americas. The extract is commercially available from a wide range of sources (see International Cosmetic Ingredient Dictionary and Handbook, 12th edition, volume 2, page 1731 (2008), which is incorporated by reference).

B. Amounts of Ingredients

It is contemplated that the compositions of the present invention can include any amount of the ingredients discussed in this specification. The compositions can also include any number of combinations of additional ingredients described throughout this specification (e.g., pigments, or additional cosmetic or pharmaceutical ingredients). The concentrations of the any ingredient within the compositions can vary. In non-limiting embodiments, for example, the compositions can comprise, consisting essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

C. Vehicles

The compositions of the present invention can be incorporated into all types of vehicles. Non-limiting examples include emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydro-alcoholic), anhydrous bases (such as lipsticks and powders), gels, and ointments. Variations and other appropriate vehicles will be apparent to the skilled artisan and are appropriate for use in the present invention. In certain aspects, it is important that the concentrations and combinations of the compounds, ingredients, and agents be selected in such a way that the combinations are chemically compatible and do not form complexes which precipitate from the finished product.

D. Additional Ingredients

In addition to the combination of ingredients disclosed by the inventors, the compositions can also include additional ingredients such as cosmetic ingredients and pharmaceutical active ingredients. Non-limiting examples of these additional ingredients are described in the following subsections.

1. Cosmetic Ingredients

The CTFA International Cosmetic Ingredient Dictionary and Handbook (2004 and 2008) describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as para-aminobenzoic acid ("PABA") and corresponding PABA derivatives, titanium dioxide, zinc oxide, etc.), essential oils, vitamins (e.g. A, B, C, D, E, and K), trace metals (e.g. zinc, calcium and selenium), anti-irritants (e.g. steroids and non-steroidal anti-inflammatories), botanical extracts (e.g. aloe vera, chamomile, cucumber extract, *ginkgo biloba, ginseng*, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, methyl gluceth-20, and mannitol), exfoliants, waterproofing agents (e.g., magnesium/aluminum hydroxide stearate), skin conditioning agents (e.g., aloe extracts, allantoin, bisabolol, ceramides, dimethicone, hyaluronic acid, biosaccharide gum-1, ethylhexylglycerin, pentylene glycol, hydrogenated polydecene, octyldodecyl oleate, and dipotassium glycyrrhizate). Non-limiting examples of some of these ingredients are provided in the following subsections.

a. UV Absorption Agents

UV absorption agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloyl trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidene camphor, and isopentyl 4-methoxycinnamate. Non-limiting examples of physical sunblocks include, kaolin, talc, petrolatum and metal oxides (e.g., titanium dioxide and zinc oxide).

b. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrrolidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, alanine, algae extract, aloe barbadensis, aloe-barbadensis extract, aloe barbadensis gel, *althea officinalis* extract, apricot (*prunus armeniaca*) kernel oil, arginine, arginine aspartate, *arnica montana* extract, aspartic acid, avocado (*persea gratissima*) oil, barrier sphingolipids, butyl alcohol, beeswax, behenyl alcohol, beta-sitosterol, birch (*betula alba*) bark extract, borage (*borago officinalis*) extract, butcherbroom (*ruscus aculeatus*) extract, butylene glycol, *calendula officinalis* extract, *calendula officinalis* oil, candelilla (*euphorbia* cerifera) wax, canola oil, caprylic/capric triglyceride, cardamom (*elettaria cardamomum*) oil, carnauba (*copernicia cerifera*) wax, carrot (*daucus carota sativa*) oil, castor (*ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*anthemis nobilis*) oil, cholesterol, cholesterol esters, cholesteryl hydroxystearate, citric acid, clary (*salvia sclarea*) oil, cocoa (*theobroma cacao*) butter, coco-caprylate/caprate, coconut (*cocos nucifera*) oil, collagen, collagen amino acids, corn (*zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, *eucalyptus globulus* oil, evening primrose (*oenothera biennis*) oil, fatty acids, geranium *maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*vitis vinifera*) seed oil, hazel (*corylus americana*) nut oil, hazel (*corylus avellana*) nut oil, hexylene glycol, hyaluronic acid, hybrid safflower (*carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*jasminum officinale*) oil, jojoba (*buxus chinensis*) oil, kelp, kukui (*aleurites moluccana*) nut oil, lactamide MEA, laneth-16, laneth-10 acetate, lanolin, lanolin acid, lanolin alcohol, lanolin oil, lanolin wax, lavender (*lavandula angustifolia*) oil, lecithin, lemon (*citrus medica limonum*) oil, linoleic acid, linolenic acid, macadamia *ternifolia* nut oil, maltitol, *matricaria* (*chamomilla recutita*) oil, methyl glucose sesquistearate, methylsilanol PCA, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*olea europaea*) oil, orange (*citrus aurantium dulcis*) oil, palm (*elaeis guineensis*) oil, palmitic acid, pantethine, panthenol, panthenyl ethyl ether, paraffin, PCA, peach (*prunus persica*) kernel oil, peanut (*arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG-40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (*mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinol palmitate, rice (*oryza sativa*) bran oil, RNA, rosemary (*rosmarinus officinalis*) oil, rose oil, safflower (*carthamus tinctorius*) oil, sage (*salvia officinalis*) oil, sandalwood (*santalum album*) oil, serine, serum protein, sesame (*sesamum indicum*) oil, shea butter (*butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*helianthus annuus*) seed oil, sweet almond (*prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*triticum vulgare*) germ oil, and ylang ylang (*cananga odorata*) oil.

c. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

d. Structuring Agents

In other non-limiting aspects, the compositions of the present invention can include a structuring agent. Structuring agent, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

e. Emulsifiers

In certain aspects of the present invention, the compositions do not include an emulsifier. In other aspects, however, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, cetearyl glucoside, cetearyl alcohol, C12-13 pareth-3, PPG-2 methyl glucose ether distearate, PPG-5-ceteth-20, bis-PEG/PPG-20/20 dimethicone, ceteth-10, polysorbate 80, cetyl phosphate, potassium cetyl phosphate, diethanolamine cetyl phosphate, polysorbate 60, glyceryl stearate, PEG-100 stearate, arachidyl alcohol, arachidyl glucoside, and mixtures thereof.

f. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

g. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, *eucalyptus* oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

h. Thickening Agents

Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene, trihydroxystearin, ammonium acryloyldimethyl-taurate/vp copolymer, or a mixture thereof.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include *acacia*, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboxymethyl dextran, sodium carrageenan, tragacanth gum, xanthan gum, and mixtures thereof.

i. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal or combinations thereof.

2. Pharmaceutical Ingredients

Pharmaceutical active agents are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

E. Kits

Kits are also contemplated as being used in certain aspects of the present invention. For instance, compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions.

EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Efficacy of Ingredients

*Leontopodium alpinum* extract, *Halidrys siliquosa* extract, vegetable amino acid (navy bean), *Pinus pinaster* extract, and *Betula alba* extract have been shown to inhibit B16 melanogenesis using a bioassay that analyzes the effect of compounds on B16 melanogenesis. The endpoint of this assay is a spectrophotometric measurement of melanin production and cellular viability. A summary of these data are provided in Table 1.

TABLE 1*

| Ingredient* | % inhibition** |
| --- | --- |
| *Leontopodium alpinum* extract (1%) | −43.75 |
| *Halidrys siliquosa* extract (1%) | −35.56106 |
| Navy bean (1%) | −14.512 |
| *Pinus pinaster* extract (1%) | −38.94 |
| *Betula alba* extract (1%) | −47.47 |

*Each ingredient was obtained from the following suppliers: *Leontopodium alpinum* extract was obtained from Carrubba Inc. under the trade name Edelweiss Extract M5768. *Halidrys siliquosa* extract was obtained from Biosil under the trade name Lightoceane ®. Navy bean was obtained from Carrubba Inc. *Pinus pinaster* extract was obtained from Carrubba Inc. *Betula alba* extract was obtained from Carrubba Inc.
**Control used was Kojic Acid 10 mM. % inhibition is calculated = (pigment levels after 3 days treated-pigment level after 3 days of untreated control) 0)/pigment level after 3 days of untreated control) × 100%). Therefore, a negative (−) indicates inhibition of melanogenesis.

The procedure used to obtain the data in Table 1 included the following steps:

Grow B16 cells to subconfluence from a frozen vial in T150 tissue culture flasks. Trypsinize 1 confluent T150 and resuspend in DMEM. Seed 1% of cells in each 96 well plate (200 ul total volume). Dilute test compounds to 1% in media. Once cells reach ~20% confluence, replace media with 200 ul diluted compounds. Treat 2 wells/group. If a positive control is utilized, treat cells with 1 mM Kojic acid. Incubate cells for 5-6 days (37° C., 10% CO2). Read plate at 405 nm. Remove all media from cells. Add 100 ul diluted MTS reagent. Incubate 15-30 min (37° C., 10% CO2). Read plate at 490 nm.

*Halidrys siliquosa* extract was found to have significant effects inhibiting transfer of melanosomes using an in vitro assay that analyzes the effect of test articles on the mechanism of melanosome transfer. Melanosome transfer is the process by which melanocytes deliver melanin to keratinocytes. Melanocytes synthesize approximately 0.5 μm melanin-containing vesicles called melanosomes which are phagocytosed by keratinocytes. This bioassay mimics this process by incubating keratinocytes with fluorescent microspheres of similar size to melanosomes. Inhibition or promotion of microsphere uptake is correlated with uptake of normal melanosomes which is a critical process for skin pigmentation. A summary of these data are provided in Table 2.

TABLE 2*

| | % Inhibition of Melanosome transfer** |
| --- | --- |
| *Halidrys siliquosa* extract 0.1% | −68.1138 |
| *Halidrys siliquosa* extract 1% | −60.9831 |

*Halidrys siliquosa* extract was obtained from Biosil under the trade name Lightoceane ®.
**Control used was the untreated set of cells. % Inhibition of Melanosome transfer = ((Mean Ex/Em of Sample/Viability*)/Mean Ex/Em of untreated Control)*100 − 100. Therefore, a negative (−) indicates inhibition of melanosome transfer.

The procedure used to obtain the data in Table 2 included the following steps:

Grow HEKa cells to subconfluence from a frozen vial in 3×T75 tissue culture flasks (37° C., 5% CO2). Wash confluent T75s (P1-P3) with HBSS then trypsinize with 1.5 ml trypsin for ~4 min at 37° C. Collect cells in 4 ml TNS, then spin in 15 ml conical tubes. Resuspend in Epilife media and plate in black 96 well plate. Dilute test compounds to appropriate concentration in sterile water. Upon reaching 85% confluence replace media with 200 ml media with 20 ul diluted test compound overnight (37° C., 5% CO2). Remove media and add replace with microsphere dilution. Re-add diluted test material. Incubate overnight (37° C., 5% CO2). Wash cells 4 times with PBS. Add 100 ul PBS per well. Read Ex/Em at 480/520 on BioTek FLx800 fluorometric plate reader. Set threshold sensitivity at 65. Remove PBS and replace with 100 ul diluted MTS reagent to each well. Incubate 15-30 min (37° C., 5% CO2). Read plate at 490 nm.

Hexylresorcinol was found to have significant effects inhibiting glycation of ribose to BSA using a ribose/BSA glycation assay. A summary of these data are provided in Table 3.

TABLE 3*

| | % Inhibition of Glycation** |
| --- | --- |
| Hexylresorcinol 0.25% | −76.11066773 |
| Hexylresorcinol 0.5% | −67.86379356 |
| Hexylresorcinol 1.0% | −54.45597233 |

*Hexylresorcinol was obtained from Syntheon Limited under the trade name Synovea ® HR.
**Control used was the untreated set of cells. % Inhibition of glycation = (glycation levels of treated-glycation levels of untreated control)/glycation levels of untreated control) × 100%). Therefore, a negative (−) indicates inhibition of glycation.

The procedure used to obtain the data in Table 2 included the following steps:

Dilute 0.2M stock solution of ribose to 0.02M in phosphate buffer. Dilute 20× stock solution of test ingredient to 2× in 0.02M ribose. Dilute 1M stock solution of AMG to 0.1M in 0.02M ribose. Add 100 μl of 10% BSA solution into all wells. Add 100 μl of 0.02M ribose into control wells (ribose/BSA positive control wells). Add 100 μl of 0.1M AMG (in 0.02M ribose) into positive control wells. Add 100 μl of test ingredients (in 0.02M ribose) into test wells. Seal plate and incubate at 42° C. for 24 hrs. Read in fluorometer at 360/460 ex/em.

Example 2

In Vitro Data

Hyperpigmentation in skin is caused by an increase in melanin, the substance in the body that is responsible for color (pigment). It is characterized by age spots, dark spots and patches of pigmentation. Vegetable amino acid (aka Navy bean) which is one of the active ingredients in this formula has been suggested to have skin brightening benefits based on in vitro testing. The inventors evaluated the effects of vegetable amino acid as a key ingredient on hyperpigmentation.

The "treated" group applied Moisturizer comprising a proprietary base lotion formulation having no preservatives ("Vinny Base") with 1% vegetable amino acid at least twice a day in the morning and at night, while the "untreated" group applied Moisturizer without 1% vegetable amino acid at least twice a day in the morning and at night.

Study design: 12 week randomized, single blind study. Sample size of treatment group was 21 panelists, sample size of untreated group (control) was 9 panelists. The panelists were screened for melasma, age spots and dark spots. Visual grading was done at Day 0 and Weeks 4, 8, and 12 by Hanh Pham. Facial photographs were taken at Day 0 and Weeks 4, 8, and 12 using Clarity Pro. Each panelist was asked to use the test product as the only facial product for 12 weeks. Basic Moisturizer and SPF 30 Sunscreen were provided, each of which comprised a Vinny Base (i.e., a proprietary base lotion formulation having no preservatives).

Visual Grading

The parameters used included:
Uneven Skin Tone: Assessment of the overall uniformity of skin color (inclusive of both pigment & blotchiness).
Discrete Pigment: Distinct uniform areas of darker pigment, for instance "age" or brown spots; freckles.
Mottled Pigment: Dark blotches that were larger and more irregular in size and shape than discrete pigmentation. These areas tend to become darker with sun exposure.
Scale: Global Photo aging Scale (0 to 9), where None (0), Mild (1,2,3), Moderate (4,5,6), and Severe (7,8,9).
Instrumental Evaluation: The Clarity™ Pro Advanced Skin Advisor System was used. The Clarity™ Pro is an imaging system with multispectral lighting for surface and sub-surface skin analysis. This imaging system utilizes patented facial recognition technology to analyze various skin features such as pigmentation, wrinkles, redness and acne. Clarity™ Pro was purchased in from BTBP Inc. The Pigmentation feature was utilized to analyze the images in this study. This features comprises of Brightness intensity, Pigmentation contrast and Pigmentation variation. Full face photographs were captured—frontal and 45° lateral images (left and right) in multispectral lighting. Images were analyzed for Brightness intensity, Pigment variation and Pigment contrast. VISIA-CR Canfield Imaging System was used as a backup, and full face photographs captured—frontal images were captured only in standard and cross polarized lighting. Images visually assessed for improvement in skin pigmentation.

Key Findings

Visual Grading Assessment: After 12 weeks, there was a significant improvement seen in the treated group (with vegetable amino acid) when compared to baseline. After 8 weeks, there was a significant difference observed between the treated and untreated group for Mottled pigment only.

Uneven skin tone (FIG. 1): There was significant improvement in the treated group at weeks 4, 8 and 12 when compared to baseline. There was significant improvement in the untreated group at week 4 when compared to baseline. There was no significant difference observed between the treated and untreated groups at all time points.

Figure 2:
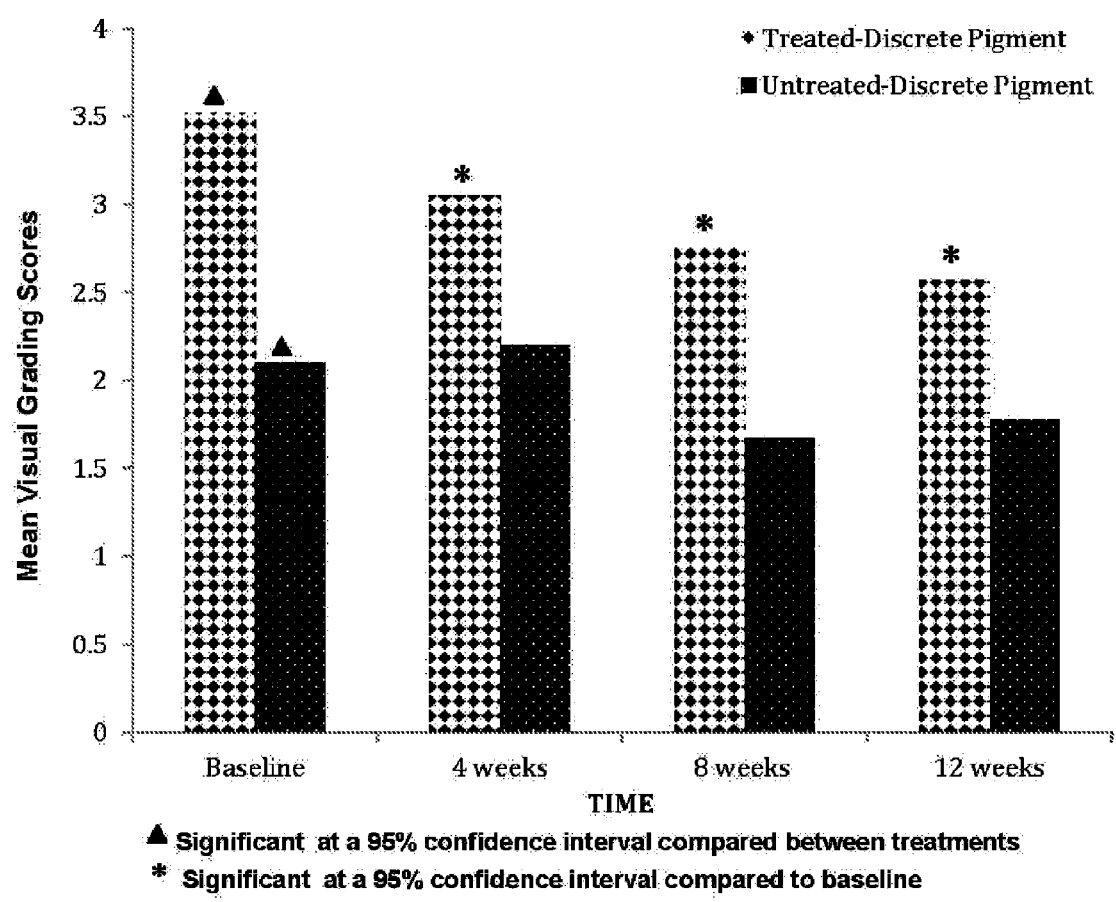
FIG. 2 Results of the visual grading of the treated and untreated groups for discrete pigment at baseline and 4, 8, and 12 weeks.

Discrete Pigment (FIG. 2): There was significant improvement in the treated group at weeks 4, 8 and 12 when compared to baseline. There was no significant improvement in the untreated group at all time points when compared to baseline. There was a significant difference observed between the treated and untreated groups at Baseline.

Figure 3:
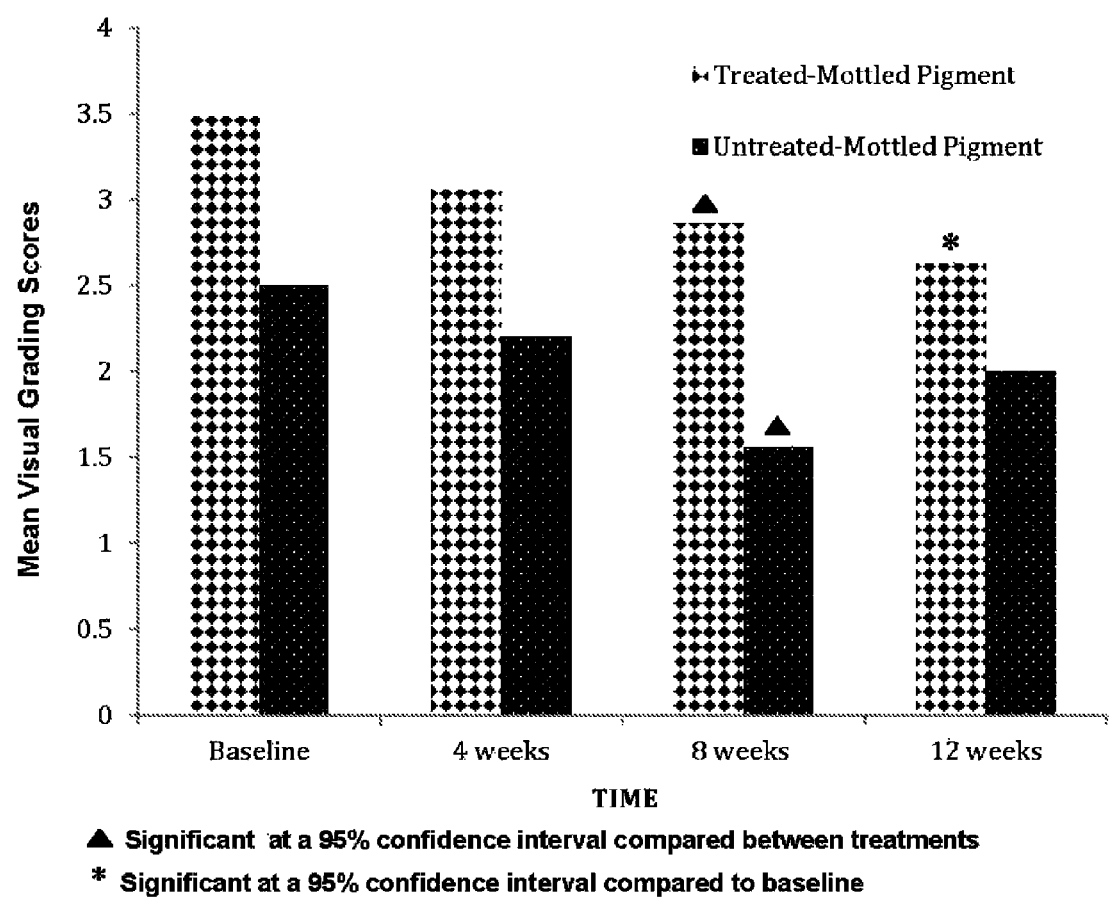
FIG. 3 Results of the visual grading of the treated and untreated groups for mottled pigment at baseline and 4, 8, and 12 weeks.

Mottled Pigment (FIG. 3): There was significant improvement in the treated group at week 12 when compared to baseline. There was no significant improvement in the untreated group at all time points. There was a significant difference observed between the treated and untreated groups at week 8.

Figure 4:
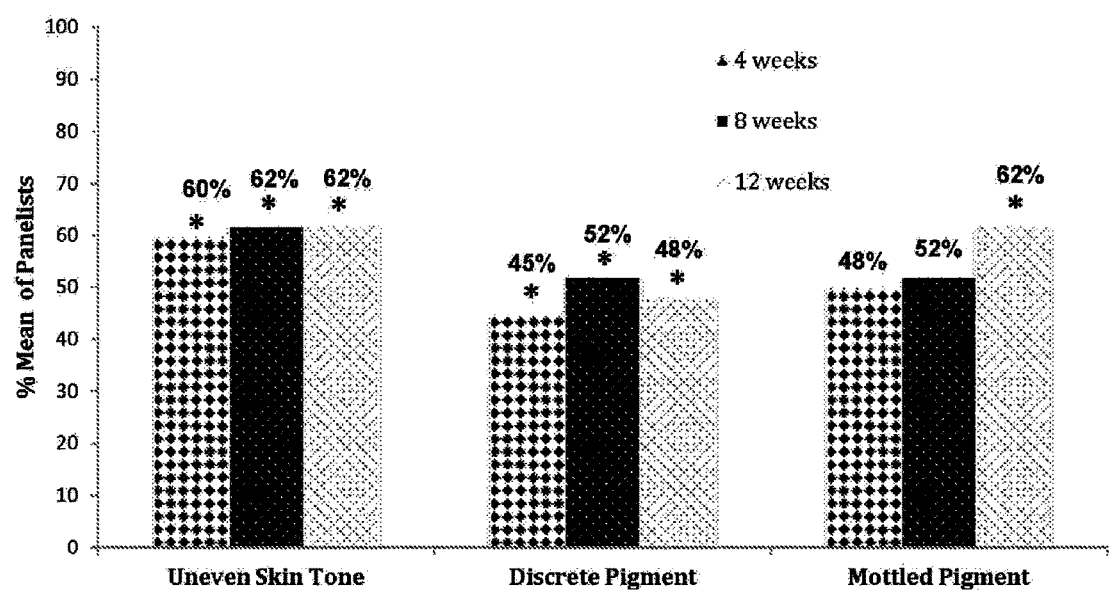
FIG. 4 Mean percentage of panelists with visual grading showing improvement over 12 weeks for the treated group.

Mean Percentage of Panelists showing Improvement over 12 weeks—Treated (FIG. 4). A significant number of panelists showed improvement in uneven skin tone at weeks 4, 8 and 12 as compared to baseline, a significant number of panelists showed improvement in discrete pigment at weeks 4, 8 and 12 as compared to baseline, and a significant number of panelists showed improvement in mottled pigment at week 12 as compared to baseline.

A significant number of panelists showed improvement in uneven skin tone at week 4 as compared to baseline in the untreated group, and the mean percentage of panelists showing improvement in discrete and mottled pigment was not significant at all time points compared to baseline.

Clarity Pro Analysis: After 12 weeks, there was a significant improvement seen in the treated group when compared to baseline. There was no significant difference observed between the treated and untreated group at all time points for all features. Overall, results obtained from visual grading assessment and quantitative Clarity Pro pigmentation analysis are consistent with the images.

Figure 5:
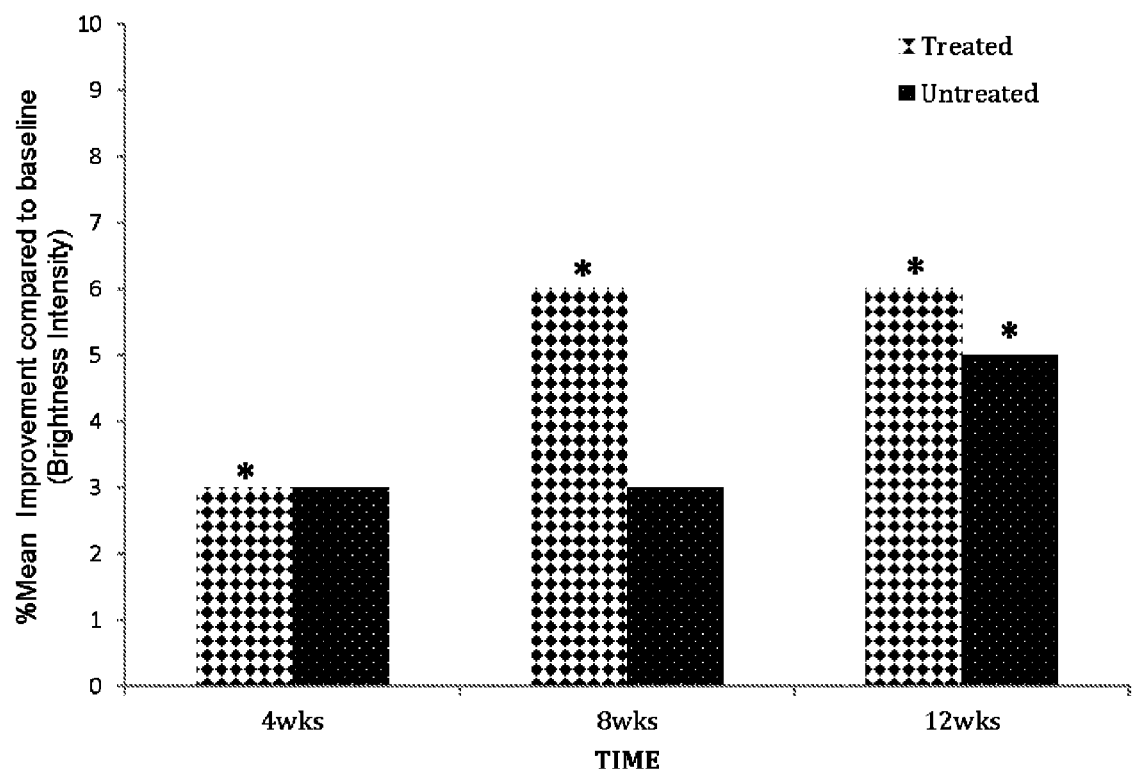
FIG. 5 Results of the Clarity™ Pro pigmentation results of the treated and untreated groups for brightness intensity at 4, 8, and 12 weeks.

Brightness Intensity (FIG. 5): There was significant improvement in the treated group at weeks 4, 8 and 12 when compared to baseline. There was significant improvement in the untreated group at week 12 when compared to baseline. There was no significant difference between the treated and untreated groups at all time points.

Figure 6:
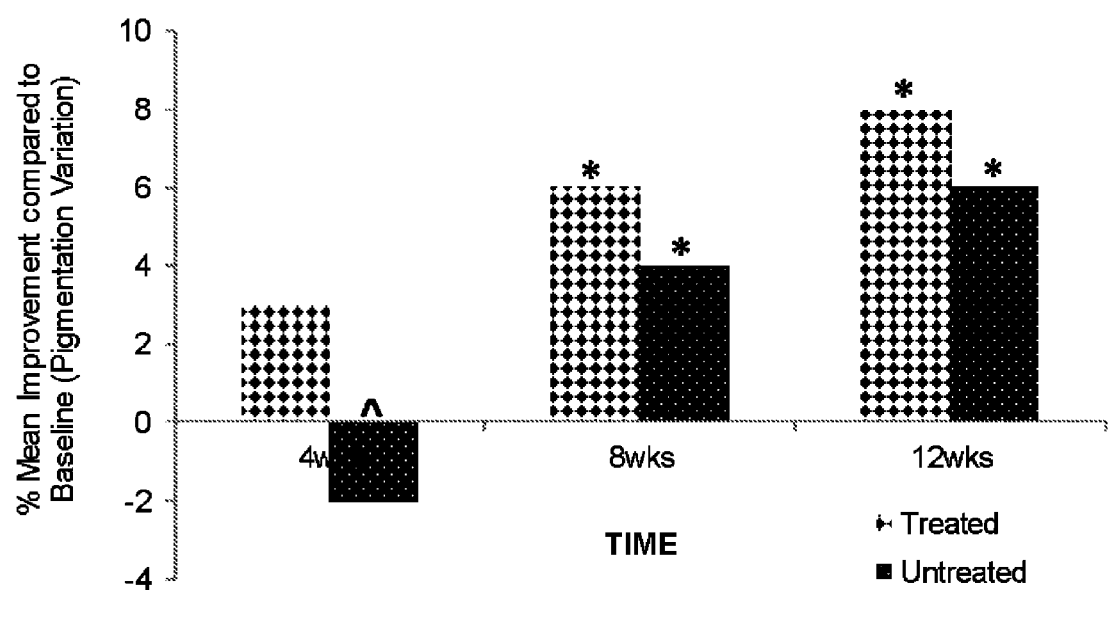
FIG. 6 Results of the Clarity™ Pro pigmentation results of the treated and untreated groups for pigmentation variation at 4, 8, and 12 weeks.

Pigmentation Variation (FIG. 6): There was significant improvement in the treated group at weeks 8 and 12 when compared to baseline. There was significant improvement in the untreated group at weeks 8 and 12 when compared to baseline. There was significant worsening in the untreated group at week 4 when compared to baseline. There was no significant difference observed between the treated and untreated groups at all time points.

Figure 7:
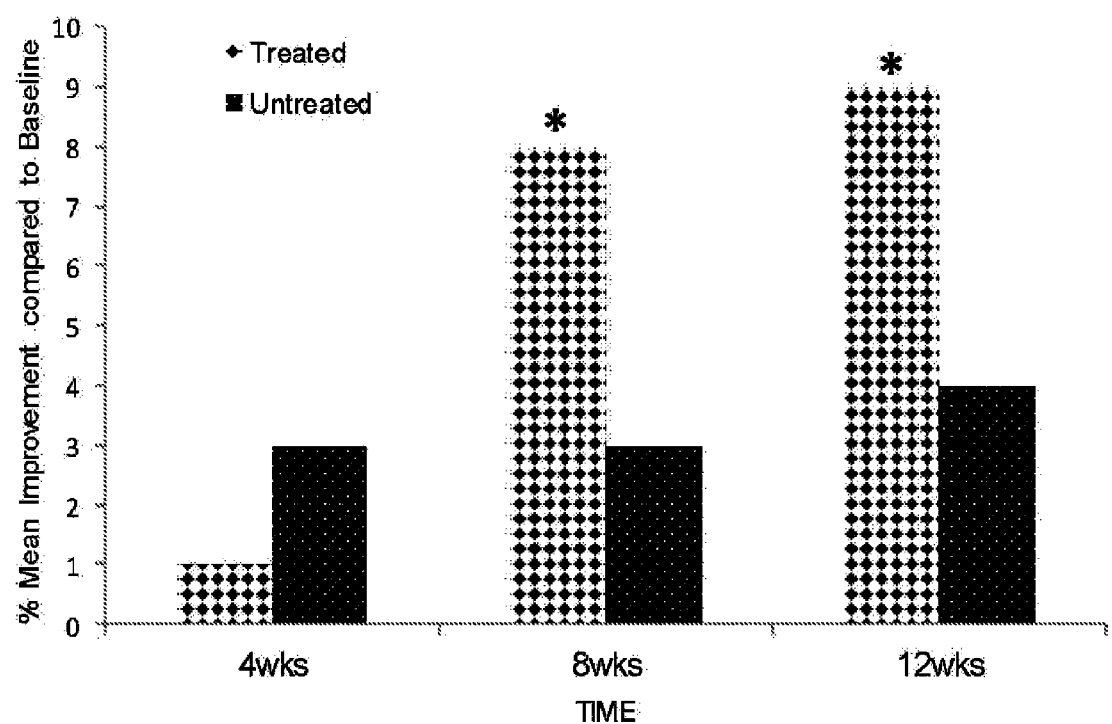
FIG. 7 Results of the Clarity™ Pro pigmentation results of the treated and untreated groups for pigment contrast at 4, 8, and 12 weeks.

Pigmentation Contrast (FIG. 7): There was significant improvement in the treated group at weeks 8 and 12 when compared to baseline. There was no significant improvement in the untreated group at all time points when compared to baseline. There was no significant difference observed between the treated and untreated groups at all time points.

Figure 8:
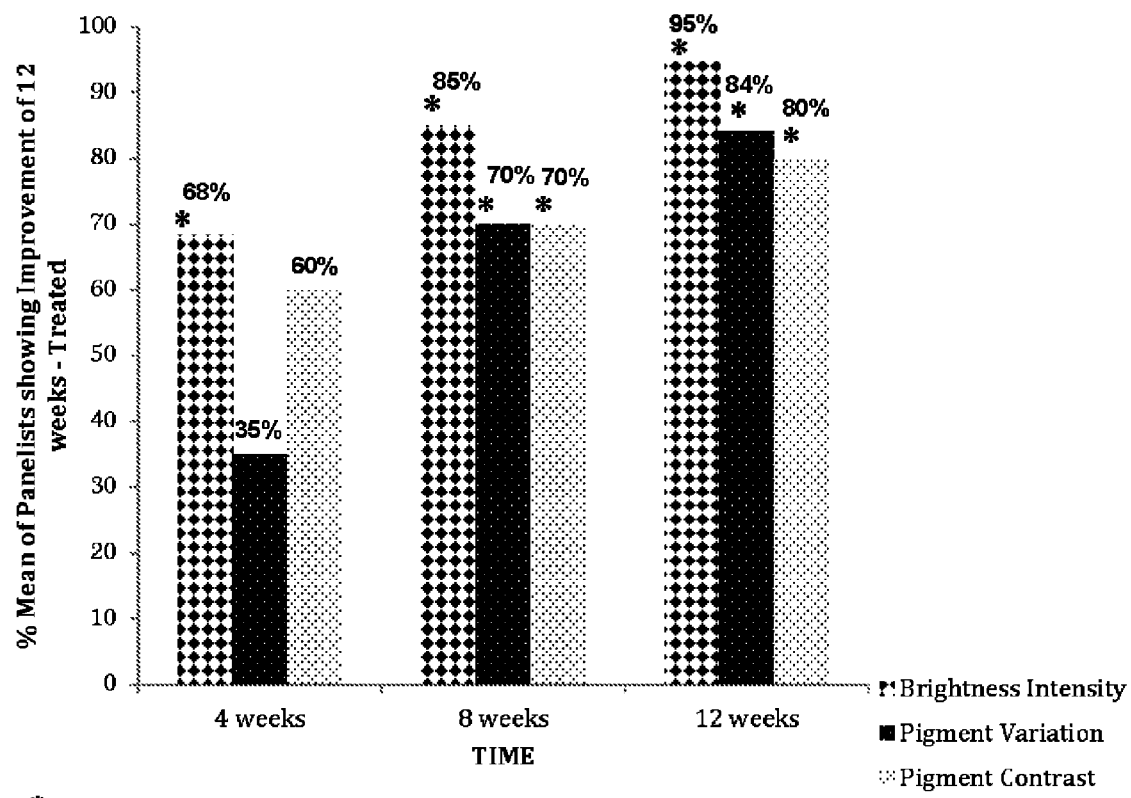
FIG. 8 Mean percentage of panelists with Clarity™ Pro pigmentation results showing improvement over 12 weeks for the treated group.

Mean Percentage of panelists showing Improvement over 12 weeks—Treated (FIG. 8). A significant number of panelists showed improvement in brightness intensity at all time points as compared to baseline, and a significant number of panelists showed improvement in pigment variation and pigment contrast at weeks 8 and 12 as compared to baseline.

Figure 9:
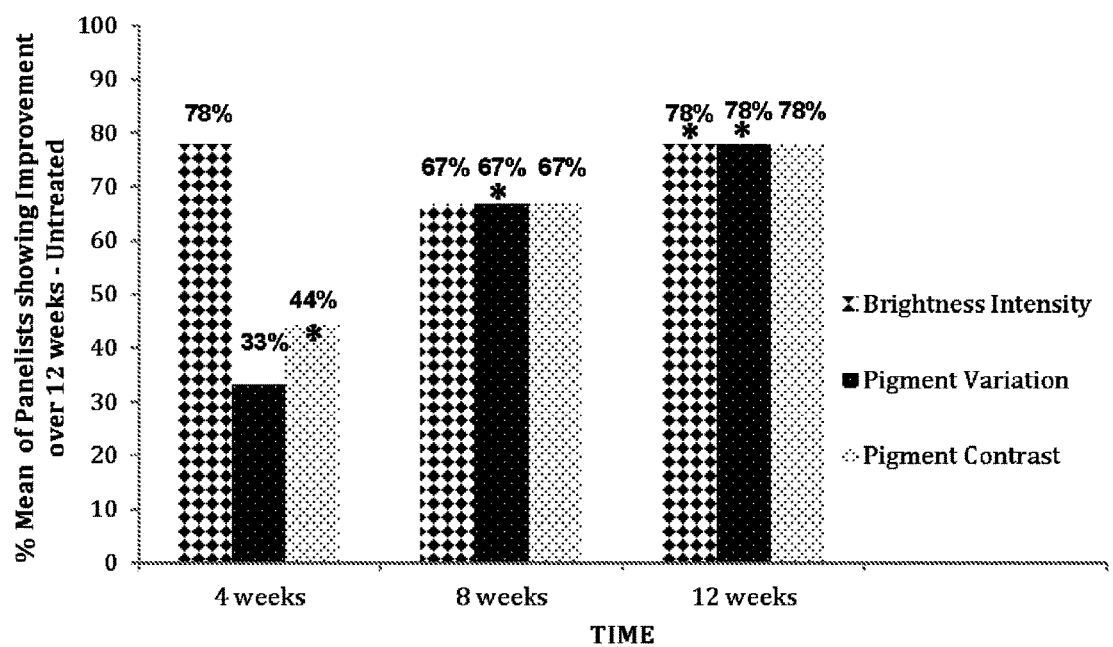
FIG. 9 Mean percentage of panelists with Clarity™ Pro pigmentation results showing improvement over 12 weeks for the untreated group.

Mean Percentage of panelists showing Improvement over 12 weeks—Untreated (FIG. 9). A significant number of panelists showed improvement in brightness intensity at week 4 as compared to baseline, a significant number of panelists showed improvement in pigment variation at week 8 as compared to baseline, and a significant number of panelists showed improvement in pigment contrast at weeks 8 and 12 as compared to baseline.

CONCLUSIONS

Uneven skin tone and discrete pigment: There was a significant improvement observed in the treated group at all time points over 12 weeks as compared to baseline.

Mottled pigment: There was a significant improvement observed at week 12 for the treated group as compared to baseline.

Brightness intensity (skin lightening): There was a significant improvement observed in the treated group at all time points over 12 weeks as compared to baseline. Pigment Variation (overall skin tone evenness) and Pigment Contrast (darkness of pigmentation): There was a significant improvement observed in the treated group at weeks 8 and 12 as compared to baseline.

Example 3

Formulations

Formulations having the ingredients from Example 1 were prepared as serums (Table 4 and Table 5), an eye cream (Table 6), a face freshener (Table 7), a moisturizer (Table 8), a night cream and a whitening cream (Table 9), a face and/or eye mask cloth (Table 10), a facial mask (Table 11), and a cleanser (Table 12).

TABLE 4*

| Ingredient | % Concentration (by weight) |
|---|---|
| *Leontopodium alpinum* extract | 0.01 |
| *Halidrys siliquosa* extract | 0.3 |
| vegetable amino acids | 0.3 |
| niacinamide | 2 |
| hexylresorcinol | 0.3 |
| *Pinus pinaster* extract | 0.01 |
| *Betula alba* extract | 0.01 |
| water | 78 |
| butylene glycol | 5 |
| glycerin | 4 |
| silica | 3 |
| cyclopentasiloxane | 3 |
| dimethicone | 2 |
| disodium EDTA | 0.3 |
| caprylyl glycol | 0.3 |
| 1,2-hexanediol | 0.2 |
| hydroxypropyl cyclodextrin | 0.07 |
| potassium sorbate | 0.02 |
| Excipients** | q.s. |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition.
**Excipients were added to modify the rheological properties of the composition. Alternatively, the amount of water can be varied so long as the amount of water in the composition is at least 60% w/w, and preferably between 70 to 80% w/w.

TABLE 5*

| Ingredient | % Concentration (by weight) |
|---|---|
| *Leontopodium alpinum* extract | 0.01 |
| *Halidrys siliquosa* extract | 0.3 |
| vegetable amino acids | 0.3 |
| niacinamide | 2 |
| hexylresorcinol | 0.25 |
| *Pinus pinaster* extract | 0.01 |
| *Betula alba* extract | 0.01 |
| water | 78 |
| butylene glycol | 5 |
| glycerin | 4 |
| silica | 3 |
| cyclopentasiloxane | 3 |
| dimethicone | 2 |
| disodium EDTA | 0.3 |
| caprylyl glycol | 0.3 |
| 1,2-hexanediol | 0.2 |
| hydroxypropyl cyclodextrin | 0.07 |
| potassium sorbate | 0.02 |
| ammonium acryloyldimethyltaurate/VP copolymer | 0.4 |
| polysorbate 20 | 0.3 |

TABLE 5*-continued

| Ingredient | % Concentration (by weight) |
|---|---|
| acrylates/C10-30 alkyl acrylate crosspolymer | 0.2 |
| triethanolamine | 0.2 |
| xanthan gum | 0.1 |
| *Opuntia tuna* fruit extract (optional) | 0.0005 |
| Excipients** | q.s. |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition.
**Excipients were added to modify the rheological properties of the composition. Alternatively, the amount of water can be varied so long as the amount of water in the composition is at least 60% w/w, and preferably between 70 to 80% w/w.

TABLE 6*

| Ingredient | % Concentration (by weight) |
|---|---|
| *Leontopodium alpinum* extract | 0.01 |
| *Halidrys siliquosa* extract | 0.3 |
| vegetable amino acids | 0.3 |
| niacinamide | 2 |
| *Albizia julibrissin* bark extract | 1 |
| water | 75 |
| glycerin | 11 |
| dimethicone | 4 |
| octyldodecanol | 0.7 |
| triethanolamine | 0.7 |
| polyacrylamide | 0.7 |
| disodium EDTA | 0.1 |
| laureth-7 | 0.1 |
| cyclohexasiloxane | 0.03 |
| sodium benzoate | 0.01 |
| iodopropynyl butylcarbamate | 0.01 |
| Excipients** | q.s. |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition.
**Excipients were added to modify the rheological properties of the composition. Alternatively, the amount of water can be varied so long as the amount of water in the composition is at least 60% w/w, and preferably between 70 to 80% w/w.

TABLE 7*

| Ingredient | % Concentration (by weight) |
|---|---|
| *Opuntia tuna* fruit extract (optional) | 0.001 |
| *Leontopodium alpinum* extract | 0.01 |
| *Halidrys siliquosa* extract | 0.3 |
| niacinamide | 1 |
| water | 78 |
| butylene glycol | 12 |
| biosaccharide gum-1 | 3 |
| glycerin | 1 |
| PPG-5-ceteth-20 | 0.8 |
| phenoxyethanol | 0.5 |
| bis-PEG/PPG-20/20 dimethicone | 0.3 |
| hydroxypropyl cyclodextrin | 0.1 |
| benzyl alcohol | 0.1 |
| Excipients** | q.s. |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition.
**Excipients were added to modify the rheological properties of the composition. Alternatively, the amount of water can be varied so long as the amount of water in the composition is at least 60% w/w, and preferably between 70 to 80% w/w.

TABLE 8*

| Ingredient | % Concentration (by weight) |
| --- | --- |
| *Leontopodium alpinum* extract | 0.01 |
| *Halidrys siliquosa* extract | 0.3 |
| vegetable amino acids | 0.3 |
| *Lentinus edodes* mycelium extract | 1 |
| niacinamide | 2 |
| water | 58 |
| isononyl isononanoate | 5 |
| glycerin | 5 |
| octisalate | 5 |
| alcohol denatured | 4 |
| octocrylene | 3 |
| avobenzone | 3 |
| butylene glycol | 2 |
| cyclopentasiloxane | 2 |
| cetearyl glucoside | 2 |
| cetyl alcohol | 1 |
| dimethicone | 1 |
| glyceryl stearate | 1 |
| PEG-100 stearate | 1 |
| phenoxyethanol | 1 |
| caprylyl glycol | 0.4 |
| ammonium acryloyldimethyltaurate/vp copolymer | 0.4 |
| magnesium aluminum silicate | 0.4 |
| xanthan gum | 0.2 |
| disodium EDTA | 0.1 |
| Excipients** | q.s. |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition.
**Excipients were added to modify the rheological properties of the composition. Alternatively, the amount of water can be varied so long as the amount of water in the composition is at least 50% w/w, and preferably between 55 to 65% w/w.

TABLE 9*

| Ingredient | % Concentration (by weight) |
| --- | --- |
| *Opuntia tuna* fruit extract (optional) | 0.001 |
| *Leontopodium alpinum* extract | 0.01 |
| *Halidrys siliquosa* extract | 0.3 |
| vegetable amino acids | 0.3 |
| *Lentinus edodes* mycelium extract | 1 |
| niacinamide | 2 |
| water | 64 |
| petrolatum | 7 |
| glycerin | 6 |
| octyldodecyl oleate | 3 |
| pentylene glycol | 3 |
| hydrogenated polydecene | 2 |
| glyceryl stearate | 2 |
| arachidyl alcohol | 1 |
| PEG-100 stearate | 1 |
| ammonium acryloyldimethyltaurate/vp copolymer | 1 |
| cetearyl alcohol | 1 |
| benzyl alcohol | 1 |
| synthetic wax | 0.6 |
| behenyl alcohol | 0.6 |
| cetearyl glucoside | 0.5 |
| microcrystalline wax/cire microcristalline | 0.4 |
| phenoxyethanol | 0.4 |
| arachidyl glucoside | 0.3 |
| xanthan gum | 0.3 |
| ceteareth-20 | 0.2 |
| disodium EDTA | 0.2 |
| tocopheryl acetate | 0.1 |
| triethanolamine | 0.1 |
| Excipients** | q.s. |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition.
**Excipients were added to modify the rheological properties of the composition. Alternatively, the amount of water can be varied so long as the amount of water in the composition is at least 60% w/w, and preferably between 60 to 70% w/w.

TABLE 10*

| Ingredient | % Concentration (by weight) |
| --- | --- |
| *Opuntia tuna* fruit extract (optional) | 0.0005 |
| *Leontopodium alpinum* extract | 0.01 |
| *Halidrys siliquosa* extract | 0.3 |
| vegetable amino acids | 0.3 |
| *Lentinus edodes* mycelium extract | 0.1 |
| niacinamide | 2 |
| water | 73 |
| glycerin | 8.2 |
| butylene glycol | 5 |
| divinyldimethicone/dimethicone copolymer | 3 |
| methyl gluceth-20 | 3 |
| dimethicone | 1 |
| biosaccharide gum-1 | 1 |
| phenoxyethanol | 0.5 |
| dimethicone/vinyl dimethicone crosspolymer | 0.5 |
| triethanolamine | 0.2 |
| acrylates/C10-30 alkyl acrylate crosspolymer | 0.2 |
| panthenol | 0.2 |
| C12-13 pareth-23 | 0.2 |
| C12-13 pareth-3 | 0.2 |
| disodium EDTA | 0.1 |
| dipotassium glycyrrhizate | 0.1 |
| xanthan gum | 0.1 |
| Excipients** | q.s. |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition.
**Excipients were added to modify the rheological properties of the composition.
The composition is a liquid that may be applied to a facial cloth in a foil packet.

TABLE 11*

| Ingredient | % Concentration (by weight) |
| --- | --- |
| *Leontopodium alpinum* extract | 0.01 |
| *Halidrys siliquosa* extract | 0.3 |
| vegetable amino acids | 0.3 |
| *Lentinus edodes* mycelium extract | 1 |
| niacinamide | 2 |
| water | 67 |
| glycerin | 12.3 |
| titanium dioxide | 7 |
| butylene glycol | 5 |
| biosaccharide gum-1 | 1 |
| polyacrylamide | 0.9 |
| hydrolyzed jojoba esters | 0.8 |
| propylene glycol | 0.6 |
| C13-14 isoparaffin | 0.4 |
| diazolidinyl urea | 0.3 |
| sodium polyacrylate | 0.2 |
| benzyl alcohol | 0.2 |
| laureth-7 | 0.1 |
| jojoba esters | 0.1 |

TABLE 11*-continued

| Ingredient | % Concentration (by weight) |
|---|---|
| methylparaben | 0.1 |
| Excipients** | q.s. |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition.
**Excipients were added to modify the rheological properties of the composition.

TABLE 12*

| Ingredient | % Concentration (by weight) |
|---|---|
| *Opuntia tuna* fruit extract (optional) | 0.0005 |
| *Leontopodium alpinum* extract | 0.001 |
| *Halidrys siliquosa* extract | 0.03 |
| vegetable amino acids | 0.01 |
| water | 28 |
| glycerin | 20 |
| potassium stearate | 18 |
| dipropylene glycol | 6.8 |
| sorbitol | 4.7 |
| potassium myristate | 3.3 |
| myristic acid | 3 |
| glyceryl stearate SE | 2.5 |
| PEG-60 glyceryl isostearate | 2.5 |
| stearic acid | 2.1 |
| sodium methyl cocoyl taurate | 1.7 |
| PEG-32 | 1.4 |
| potassium laurate | 1.3 |
| glycol stearate | 1 |
| benzyl alcohol | 0.9 |
| PEG-6 | 0.9 |
| polyquaternium-7 | 0.5 |
| lauric acid | 0.3 |
| sodium chloride | 0.3 |
| PEG-4 laurate | 0.2 |
| ethylene brassylate | 0.1 |
| Excipients** | q.s. |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition.
**Excipients were added to modify the rheological properties of the composition.

All of the skin-active ingredients, compositions, or methods disclosed and claimed in this specification can be made and executed without undue experimentation in light of the present disclosure. While the skin-active ingredients, compositions, or methods of this invention have been described in terms of particular embodiments, it will be apparent to those of skill in the art that variations may be applied to the skin-active ingredients, compositions, or methods and in the steps or in the sequence of steps of the method described herein without departing from the concept, spirit and scope of the invention.

The invention claimed is:

1. A method for whitening or lightening skin, the method comprising topically applying to skin in need thereof a composition comprising an effective amount of *Leontopodium alpinum* extract, *Halidrys siliquosa* extract, aqueous navy bean extract, and niacinamide, wherein the composition whitens or lightens the skin, and wherein the navy bean extract comprises amino acids.

2. The method of claim 1, wherein the composition comprises 0.001 to 0.1% by weight of *Leontopodium alpinum* extract, 0.1 to 1.0% by weight of *Halidrys siliquosa* extract, 0.1 to 1.0% by weight of aqueous navy bean extract, and 1 to 5% by weight of niacinamide.

3. The method of claim 1, wherein the composition further includes water.

4. The method of claim 3, wherein the composition comprises 55 to 80% by weight of water.

5. The method of claim 1, wherein the composition further includes *Opuntia tuna* fruit extract.

6. The method of claim 5, wherein the composition comprises 0.0001 to 0.015% by weight of *Opuntia tuna* fruit extract.

7. The method of claim 1, wherein the composition further includes:
hexylresorcinol;
*Pinus pinaster* extract; and
*Betula alba* extract,
wherein the composition also inhibits glycation.

8. The method of claim 7, wherein the composition includes:
0.1 to 0.5% by weight of hexylresorcinol;
0.001 to 0.1% by weight of *Pinus pinaster* extract; and
0.001 to 0.1% by weight of *Betula alba* extract.

9. The method of claim 7, wherein the composition further includes:
butylene glycol;
glycerin;
silica;
cyclopentasiloxane;
dimethicone;
disodium EDTA;
caprylyl glycol;
1, 2-hexanediol;
hydroxypropyl cyclodextrin; and
potassium sorbate.

10. The method of claim 9, wherein the composition includes:
3 to 6% by weight of butylene glycol;
3 to 6% by weight of glycerin;
1 to 5% by weight of silica;
1 to 4% by weight of cyclopentasiloxane;
1 to 3% by weight of dimethicone;
0.1 to 0.5% by weight of disodium EDTA;
0.1 to 0.5% by weight of caprylyl glycol;
0.1 to 0.5% by weight of 1, 2-hexanediol;
0.01 to 0.5% by weight of hydroxypropyl cyclodextrin; and
0.001 to 0.05% by weight of potassium sorbate.

11. The method of claim 9, wherein the composition further includes:
ammonium acryloyldimethyltaurate/VP copolymer;
polysorbate 20;
acrylates/C10-30 alkyl acrylate crosspolymer;
triethanolamine; and
xanthan gum.

12. The method of claim 11, wherein the composition includes:
0.1 to 1% by weight of ammonium acryloyldimethyltaurate/VP copolymer;
0.1 to 0.5% by weight of polysorbate 20;
0.1 to 0.5% by weight of acrylates/C10-30 alkyl acrylate crosspolymer;
0.1 to 0.5% by weight of triethanolamine; and
0.01 to 0.2% by weight of xanthan gum.

13. The method of claim 1, wherein the composition further includes *Albizia julibrissin* bark extract.

14. The method of claim 13, wherein the composition includes 0.5 to 2.0% by weight of *Albizia julibrissin* bark extract.

15. The method of claim 13, wherein the composition further includes:
glycerin;
dimethicone;
octyldodecanol;
triethanolamine;
polyacrylamide;
disodium EDTA;
laureth-7;
cyclohexasiloxane;
sodium benzoate; and
iodopropynyl butylcarbamate.

16. The method of claim 15, wherein the composition includes:
8 to 15% by weight of glycerin;
3 to 6% by weight of dimethicone;
0.1 to 1.5% by weight of octyldodecanol;
0.1 to 1.5% by weight of triethanolamine;
0.1 to 1.5% by weight of polyacrylamide;
0.01 to 0.2% by weight of disodium EDTA;
0.01 to 0.2% by weight of laureth-7;
0.01 to 0.2% by weight of cyclohexasiloxane;
0.001 to 0.2% by weight of sodium benzoate; and
0.001 to 0.2% by weight of iodopropynyl butylcarbamate.

17. The method of claim 1, wherein the composition further includes hydrolyzed *Candida saitoana* extract.

18. The method of claim 1, wherein the composition further includes *Lentinus edodes* mycelium extract.

19. The method of claim 18, wherein the composition comprises 0.01 to 3% by weight of *Lentinus edodes* mycelium extract.

20. The method of claim 18, wherein the composition further includes:
isononyl isononanoate;
glycerin;
octisalate;
alcohol denatured;
octocrylene;
avobenzone;
butylene glycol;
cyclopentasiloxane;
cetearyl glucoside;
cetyl alcohol;
dimethicone;
glyceryl stearate;
PEG-100 stearate;
phenoxyethanol;
caprylyl glycol;
ammonium acryloyldimethyltaurate/vp copolymer;
magnesium aluminum silicate;
xanthan gum; and
disodium EDTA.

21. The method of claim 20, wherein the composition includes:
3 to 9% by weight of isononyl isononanoate;
3 to 9% by weight of glycerin;
3 to 9% by weight of octisalate;
2 to 8% by weight of alcohol denatured;
1 to 7% by weight of octocrylene;
1 to 7% by weight of avobenzone;
0.5 to 6% by weight of butylene glycol;
0.5 to 6% by weight of cyclopentasiloxane;
0.5 to 6% by weight of cetearyl glucoside;
0.1 to 4% by weight of cetyl alcohol;
0.1 to 4% by weight of dimethicone;
0.1 to 4% by weight of glyceryl stearate;
0.1 to 4% by weight of PEG-100 stearate;
0.1 to 4% by weight of phenoxyethanol;
0.1 to 1.5% by weight of caprylyl glycol;
0.1 to 1.5% by weight of ammonium acryloyldimethyltaurate/vp copolymer;
0.1 to 1.5% by weight of magnesium aluminum silicate;
0.1 to 0.5% by weight of xanthan gum; and
0.01 to 0.5% by weight of disodium EDTA.

22. The method of claim 18, wherein the composition further includes:
petrolatum;
glycerin;
octyldodecyl oleate;
pentylene glycol;
hydrogenated polydecene;
glyceryl stearate;
arachidyl alcohol;
PEG-100 stearate;
ammonium acryloyldimethyltaurate/vp copolymer;
cetearyl alcohol;
benzyl alcohol;
synthetic wax;
behenyl alcohol;
cetearyl glucoside;
microcrystalline wax;
phenoxyethanol;
arachidyl glucoside;
xanthan gum;
ceteareth-20;
disodium EDTA;
tocopheryl acetate; and
triethanolamine.

23. The method of claim 22, wherein the composition includes:
5 to 11% by weight of petrolatum;
3 to 11% by weight of glycerin;
1 to 7% by weight of octyldodecyl oleate;
1 to 7% by weight of pentylene glycol;
0.5 to 6% by weight of hydrogenated polydecene;
0.5 to 6% by weight of glyceryl stearate;
0.1 to 4% by weight of arachidyl alcohol;
0.1 to 4% by weight of PEG-100 stearate;
0.1 to 4% by weight of ammonium acryloyldimethyltaurate/vp copolymer;
0.1 to 4% by weight of cetearyl alcohol;
0.1 to 4% by weight of benzyl alcohol;
0.1 to 4% by weight of synthetic wax;
0.1 to 4% by weight of behenyl alcohol;
0.1 to 4% by weight of cetearyl glucoside;
0.1 to 1.5% by weight of microcrystalline wax;
0.1 to 1.5% by weight of phenoxyethanol;
0.1 to 1.5% by weight of arachidyl glucoside;
0.1 to 1% by weight of xanthan gum;
0.01 to 0.5% by weight of ceteareth-20;
0.01 to 0.5% by weight of disodium EDTA;
0.01 to 0.3% by weight of tocopheryl acetate; and
0.01 to 0.3% by weight of triethanolamine.

24. The method of claim 18, wherein the composition further includes:
glycerin;
butylene glycol;
divinyldimethicone/dimethicone copolymer;
methyl gluceth-20;
dimethicone;
biosaccharide gum-1;
phenoxyethanol;
dimethicone/vinyl dimethicone crosspolymer;
triethanolamine;

acrylates/C10-30 alkyl acrylate crosspolymer;
panthenol;
C12-13 pareth-23;
C12-13 pareth-3;
disodium EDTA;
dipotassium glycyrrhizate; and
xanthan gum.

25. The method of claim 24, wherein the composition includes:
5 to 15% by weight of glycerin;
1 to 10% by weight of butylene glycol;
1 to 10% by weight of divinyldimethicone/dimethicone copolymer;
1 to 10% by weight of methyl gluceth-20;
0.1 to 5% by weight of dimethicone;
0.1 to 5% by weight of biosaccharide gum-1;
0.1 to 2% by weight of phenoxyethanol;
0.1 to 5% by weight of dimethicone/vinyl dimethicone crosspolymer;
0.1 to 1% by weight of triethanolamine;
0.1 to 1% by weight of acrylates/C10-30 alkyl acrylate crosspolymer;
0.1 to 1% by weight of panthenol;
0.05 to 0.5% by weight of C12-13 pareth-23;
0.05 to 0.5% by weight of C12-13 pareth-3;
0.01 to 0.5% by weight of disodium EDTA;
0.01 to 0.5% by weight of dipotassium glycyrrhizate; and
0.01 to 0.5% by weight of xanthan gum.

26. The method of claim 18, wherein the composition further includes:
glycerin;
titanium dioxide;
butylene glycol;
biosaccharide gum-1;
polyacrylamide;
hydrolyzed jojoba esters;
propylene glycol;
C13-14 isoparaffin;
diazolidinyl urea;
sodium polyacrylate;
benzyl alcohol;
laureth-7;
jojoba esters; and
methylparaben.

27. The method of claim 26, wherein the composition comprises:
5 to 25% by weight of glycerin;
3 to 15% by weight of titanium dioxide;
1 to 10% by weight of butylene glycol;
0.1 to 3% by weight of biosaccharide gum-1;
0.1 to 3% by weight of polyacrylamide;
0.1 to 3% by weight of hydrolyzed jojoba esters;
0.1 to 3% by weight of propylene glycol;
0.1 to 3% by weight of C13-14 isoparaffin;
0.1 to 1% by weight of diazolidinyl urea;
0.1 to 1% by weight of sodium polyacrylate;
0.05 to 0.5% by weight of benzyl alcohol;
0.05 to 0.5% by weight of laureth-7;
0.05 to 0.5% by weight of jojoba esters; and
0.05 to 0.5% by weight of methylparaben.

28. The method of claim 1, wherein the composition inhibits melanogenesis, melanosome transfer, and/or glycation.

29. The method of claim 1, wherein the composition is applied to dark spots on skin, uneven skin, and/or hyperpigmented skin.

30. The method of claim 1, wherein the composition further includes hexylresorcinol and wherein the composition further inhibits glycation.

31. The method of claim 30, wherein the composition comprises an effective amount of hexylresorcinol to inhibit glycation.

* * * * *